United States Patent [19]
Ramasamy et al.

[11] Patent Number: 5,834,466
[45] Date of Patent: Nov. 10, 1998

[54] METHOD FOR PROTECTING OF HEART BY LIMITING METABOLIC AND IONIC ABNORMALITIES DEVELOPED DURING ISCHEMIA, FOLLOWING ISCHEMIA OR RESULTING FROM ISCHEMIA

[75] Inventors: Ravichandran Ramasamy; Saul Schaefer, both of Davis, Calif.

[73] Assignee: The Regents of the University of California, Oakland, Calif.

[21] Appl. No.: 574,899

[22] Filed: Dec. 19, 1995

Related U.S. Application Data

[63] Continuation-in-part of Ser. No. 362,400, Dec. 22, 1994, abandoned.

[51] Int. Cl.⁶ .................. A61K 31/54; A61K 31/495; A61K 31/44
[52] U.S. Cl. ................. 514/227.5; 514/248; 514/356
[58] Field of Search .................... 514/356, 227.5, 514/248

[56] References Cited

U.S. PATENT DOCUMENTS

| | | | |
|---|---|---|---|
| 4,211,772 | 7/1980 | Fauran et al. | 424/180 |
| 4,466,958 | 8/1984 | Morrison | 424/127 |
| 5,023,245 | 6/1991 | Kuhrts | 514/54 |
| 5,294,641 | 3/1994 | Stanko | 514/540 |
| 5,391,551 | 2/1995 | Peterson | 514/248 |

OTHER PUBLICATIONS

CAPLUS Abstract, Lamping et al., J. Pharmacol. Exp. Ther., 231(3), 532–8 1984.

CAPLUS Abstract, Regitz, et al. Cardiovasc. Res. 15(11), 652–8,1981.

*Primary Examiner*—Raymond Henley, III
*Attorney, Agent, or Firm*—Hana Verny

[57] ABSTRACT

A therapeutic and prophylactic method for protection of heart or heart tissue by limiting metabolic and ionic abnormalities developed during, following or associated with ischemia by administering to a subject in need either a compound which reduces NADH/NAD$^+$ ratio and stimulates glycolysis to produce ATP or a compound which inhibits cotransporter of sodium-potassium-chloride.

16 Claims, 14 Drawing Sheets

■ Non Diabetic Controls
♦ Diabetic Controls
□ Bumetanide
● Bumetanide + 8 mM $K^+$
▲ 8 mM $K^+$ ■ Diabetic Controls
● Diabetic + Zopolrestat

METHOD FOR PROTECTING OF HEART BY LIMITING METABOLIC AND IONIC ABNORMALITIES DEVELOPED DURING ISCHEMIA, FOLLOWING ISCHEMIA OR RESULTING FROM ISCHEMIA

This application is a continuation-in-part of U.S. application Ser. No. 08/362,400, filed on Dec. 22, 1994 now abandoned.

BACKGROUND OF THE INVENTION

Field of Invention

The current invention concerns a method for protection of heart or heart tissue by limiting metabolic and ionic abnormalities developed during, following or associated with ischemia and resulting in damage of the heart or heart tissue. In particular, the current invention concerns the method for protecting the heart from ischemic damage caused by metabolic or ionic abnormalities by administering to a subject in need thereof either a therapeutically effective amount of a compound which reduces $NADH/NAD^+$ ratio and stimulates glycolysis to produce ATP or a therapeutically effective amount of a compound which inhibits the cotransporter of sodium-potassium-chloride. The method is either therapeutic, whereby in order to limit ischemic damage to the heart and to the heart tissue, the compound is administered to the subject immediately or as soon as possible after the ischemic event, or prophylactic, whereby the compound is administered to the subject who is at risk of developing the ischemia prior to the ischemic insult.

BACKGROUND ART AND RELATED ART DISCLOSURES

Cardiovascular disease presents a major cause of morbidity and mortality. This is particularly true for diabetic patients whose incidence of heart failure after myocardial infarction is significantly greater than for non-diabetic patients. Diabetic patients are also at increased risk for diabetic cardiomyopathy independent of coronary disease.

Previous investigations of diabetic heart vis-a-vis its vulnerability to an ischemic insult led to controversial findings. Some studies (*Circ. Res.*, 62:931 (1988) and *J. Mol. Cell. Cardiol.*, 24:411 (1992)) indicated that diabetes protects the heart from ischemia and reperfusion injury. The other studies indicated that diabetic hearts are less likely to survive an ischemic result (*Circ. Res.*, 44:322 (1979) and 62:975 (1988)). While the vulnerability of the diabetic myocardium was studied using variables such as insulin treatments or insulin and non-insulin dependency, these studies primarily concentrated on determination and measurement of the infarct size and on impairment of contractile function but not on any cellular or intracellular changes.

This was unfortunate, as there seem to be some abnormalities present in the diabetic patients at the myocyte level which increase risk of these patients during ischemia. One of these found abnormalities is alteration in ion transport and ion regulation in myocytes. These abnormalities include elevated intracellular calcium and sodium and reduced ATPase activity. Additionally, the sodium-calcium exchanger was found to be severely impaired in diabetic hearts (*Mol. Cell Biochem.*, 107:1–20 (1991)).

However, up to date, the ionic changes occurring as a response to ischemic insult in normally functioning heart or under the normal perfusion conditions, during global zero-flow ischemia, low-flow ischemia and reperfusion were not studied and/or correlated to a degree of damage developing as a result of the ischemic insult. Events leading to such metabolic or ionic abnormalities resulting in damage of the heart due to the ischemic insult was never elucidated and the possible treatment or prevention of extent of such ischemic metabolic or ionic abnormalities damage was never described.

Since the ischemic damage determines the mortality and or/survival rate of these patients, it would be highly advantageous to provide a method for preventing and limiting ischemic heart damage and/or for treatment of ischemic damage of the heart tissue.

Aldose reductase inhibitors constitute a class of compounds which have been shown to treat conditions arising from complications such as diabetic neuropathy or nephropathy, to lower lipid levels in blood of mammals, (U.S. Pat. Nos. 4,492,706 and 5,391,551) as well as to treat capillary fragility and modify evolution of diabetic cataracts (U.S. Pat. No. 4,211,772). Certain representative of aldose reductase inhibitors are compounds described in the U.S. Pat. No. 4,939,140. Aldose reductase inhibitors have not been previously connected with limiting or decreasing the extent of the ischemic damage due to metabolic and ionic abnormalities to the heart.

Furosemide and bumetanide were previously used for preservation of heart for transplantation during hypothermic ischemia (*J. Mol. Cell Cardiol.*, 25:1403 (1993). The use of these compounds limiting the extent of metabolic or ionic abnormalities in normal or diabetic hearts was not described.

It is therefore a primary objective of this invention to provide an effective method for treatment and prevention of development of ischemic damage due to metabolic and ionic abnormalities to the heart and heart tissue by providing a compound which can reduce $NADH/NAD^+$ ratio a stimulate glycolysis to produce ATP or a compound which inhibits cotransport of sodium-potassium-chloride through the myocyte wall.

All patents, publication and other cited references are hereby incorporated by reference in their entirety.

SUMMARY

One aspect of the current invention is a method for limiting or decreasing the extent of the ischemic damage due to metabolic and ionic abnormalities of the heart tissue resulting from ischemic insult.

Another aspect of the current invention is a method for limiting or decreasing the extent of the ischemic damage due to metabolic and ionic abnormalities of the heart tissue resulting from ischemic insult whereby a subject having suffered ischemic insult is treated with a therapeutical amount of a compound which reduces $NADH/NAD^+$ ratio and stimulates glycolysis to produce ATP, or with a compound which inhibits sodium-potassium-chloride immediately or as soon as possible following the ischemia.

Another aspect of the current invention is a method for limiting or decreasing the extent of the ischemic damage due to metabolic and ionic abnormalities of the heart tissue resulting from ischemic insult whereby a subject having suffered ischemic insult is treated with a therapeutical amount of an aldose reductase inhibitor, furosemide, piretanide, benzmetadine, bumetanide, toresamide, nicotinic acid, methylene blue or any pharmaceutically acceptable salt or ester thereof.

Still another aspect of the current invention is a method for providing cardioprotection by limiting metabolic or ionic abnormalities of the heart and heart tissue associated with and resulting from ischemic insult to a subject being at risk of developing such metabolic or ionic abnormalities resulting from ischemia.

Still another aspect of the current invention is a method for providing cardioprotection by limiting or decreasing the extent of the ischemic damage due to metabolic and ionic abnormalities of the heart tissue resulting from ischemic insult whereby a subject having suffered ischemic insult is treated with a therapeutical amount of a compound which reduces NADH/NAD$^+$ ratio and stimulates glycolysis to produce ATP, or with a compound which inhibits sodium-potassium-chloride prior to the ischemic insult.

Still another aspect of the current invention is a method for providing cardioprotection of the heart and heart tissue by limiting or decreasing the extent of the ischemic damage due to metabolic and ionic abnormalities of the heart tissue resulting from ischemic insult whereby a subject having suffered ischemic insult is treated with a therapeutical amount of an aldose reductase inhibitor or with a therapeutical amount of the inhibitor of cotransporter of sodium-potassium-chloride, nicotinic acid, methylene blue or any pharmaceutically acceptable salt or ester thereof.

Still yet another aspect of the current invention is a method for protecting heart and heart tissue from ischemic or post-ischemic damage associated with and resulting from ischemic event, whereby a subject having suffered ischemic event is treated with a therapeutical amount of an aldose reductase inhibitor selected from the group consisting of zopolrestat, tolrestat, epolrestat, and zenorestat or with a therapeutical amount of the inhibitor of cotransporter of sodium-potassium-chloride selected from the group consisting of furosemide, piretanide, benzmetadine, bumetanide, toresamide, or any pharmaceutically acceptable salt or ester thereof, either before, immediately after, or as soon as possible after ischemia.

Still yet another aspect is a method for protecting heart and heart tissue from metabolic and ionic abnormalities associated with and resulting from zero-flow ischemic event whereby a subject having these abnormalities is treated with a therapeutical amount of a compound which reduces NADH/NAD$^+$ ratio and stimulates glycolysis to produce ATP or with a therapeutical amount of the inhibitor of cotransporter of sodium-potassium-chloride.

DEFINITIONS

As used herein:

"Myocardial ischemia" means inadequate circulation of blood to the myocardium resulting in a lack of oxygen blood supply to the heart. Myocardial ischemia usually develops as a result of a coronary artery disease such as occlusion of coronary artery. Myocardial ischemia is a local arrest or sudden insufficiency of arterial or venous blood supply due to emboli, thrombi, vascular torsion or pressure that produces a macroscopic area of necrosis.

"Ischemic event" means any condition causing myocardial ischemia. Most common ischemic events are myocardial infarction, angina or stroke.

"Prevention of development of myocardial infarction, angina or stroke leading to myocardial ischemia" means any method and/or compound used for prevention of development of ischemia, such as, for example, prevention of development of atheromatous plaque or thrombus by providing lipid or cholesterol lowering agents, antithrombotic or anticoagulation agents, antihypertensive agents, etc.

"Prevention of development of heart damage due to metabolic or ionic abnormalities associated with and/or resulting from ischemia" means a protection of heart and heart tissue from damage caused by the metabolic and ionic abnormalities developed as a consequence of the ischemia, whether due to myocardial infarction or other causes. During the ischemic event certain area of the heart tissue is submitted to ischemia, that is to a lack of supply of oxygen to that area due to a complete stoppage (zero-flow ischemia) or substantial decrease (low-flow ischemia) of blood supply to the heart tissue via coronary vessels. When this occurs, the supply of oxygen is reduced or stopped and the myocardial tissue is damaged reversibly, if the ischemic event is short, or irreversibly, if the ischemic event is longer. The extent of the ischemic damage to the heart tissue, measured by the size of the ischemic area, particularly damage to the myocytes, heart muscle tissue cells, depends on the length of the ischemic event and whether or not the ischemia is zero-flow or low-flow ischemia, as defined below.

"Zero-flow ischemia" means ischemia or induced ischemia where there is essentially no flow of blood or perfusate through heart during the period of zero-flow ischemia.

"Low-flow ischemia" means ischemia or induced ischemia where there is low-flow of blood or perfusate through heart during the ischemic event. Clinically, low-flow ischemia means that there is some blood flow through heart during ischemia following myocardial infarction. Experimentally, the low-flow induced ischemia means slowing down the perfusate flow to approximately about 10% of the normal flow. "Inhibitor of contransport of sodium-potassium-chloride" means any compound which can substantially or completely inhibit transport of sodium-potassium-chloride through the myocyte membrane. Examples of the sodium-potassium-chloride cotransporters are furosemide, piretanide, benzmetadine, bumetanide, toresamide, or any pharmaceutically acceptable salt or ester thereof.

DETAILED DESCRIPTION OF THE INVENTION

Figure 1:
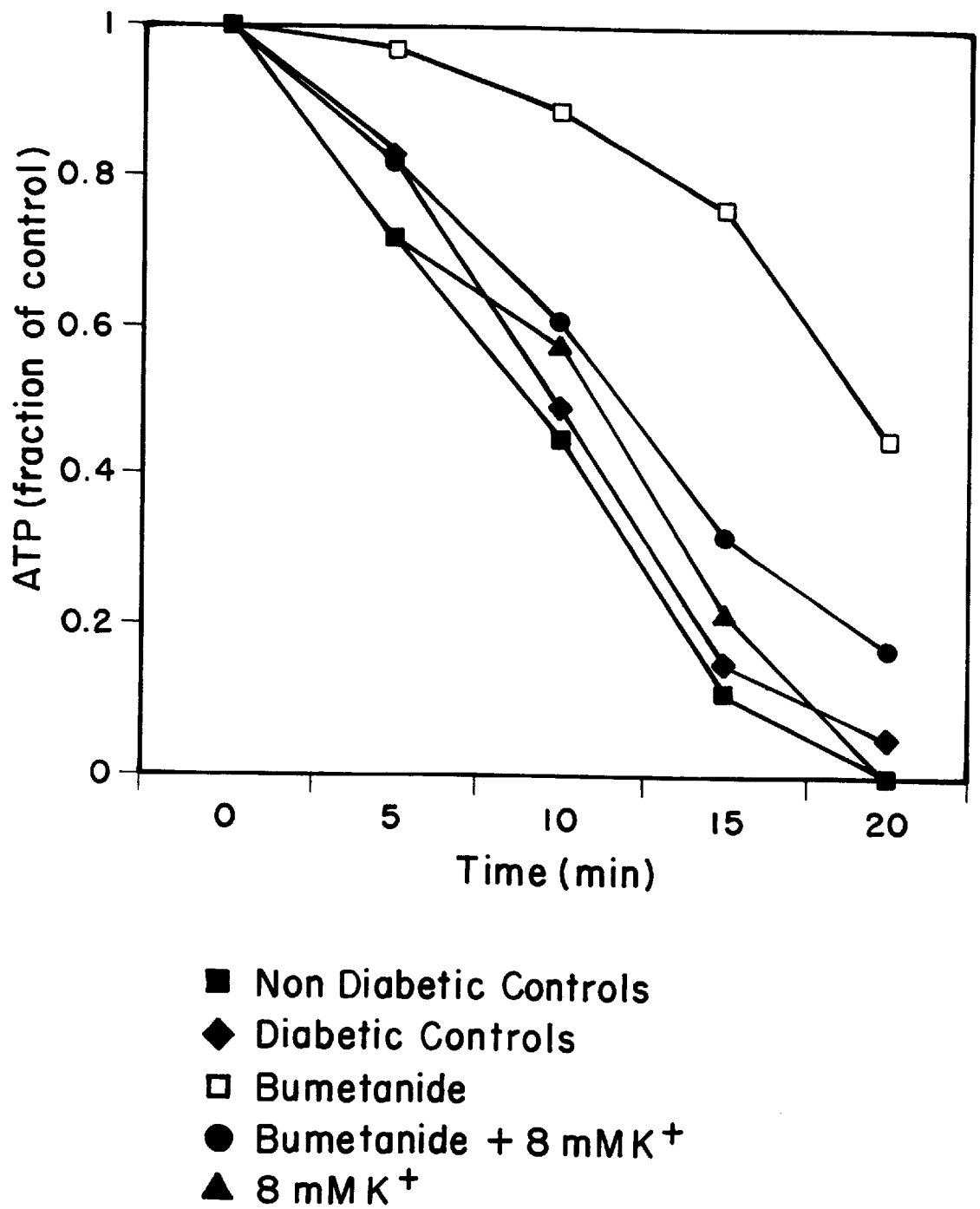
FIG. 1 depicts ATP utilization during ischemia in non-diabetic, diabetic and bumetanide treated diabetic hearts.

The current invention concerns a method for protecting heart and heart tissue from ischemic damage by limiting extent of metabolic and ionic abnormalities which develop during, following or which are associated with ischemia and which cause damage of the heart or heart tissue. The method protects the heart from damage caused by metabolic or ionic abnormalities by administering to a subject in need thereof either a therapeutically effective amount of a compound which reduces NADH/NAD$^+$ ratio and stimulates glycolysis to produce ATP, or a therapeutically effective amount of a compound which inhibits cotransporter of sodium-potassium-chloride.

The method is either therapeutic, or prophylactic. Therapeutically, the compound is administered to a subject suffering from the myocardial ischemia immediately or as soon as possible after the ischemic insult. Prophylactically, in order to limit ischemic damage to the heart and to the heart tissue from metabolic or ionic abnormalities associated with ischemia, the compound is administered to a subject who is at risk of developing the ischemia or metabolic or ionic abnormalities, prior to the ischemic insult.

The current method and treatment must be distinguished from the treatment and prevention of ischemia or myocardial infarction. The subject of this invention is not to prevent ischemia or myocardial infarction. The subject of this invention is to prevent or limit the extent of metabolic and ionic abnormalities and ultimately the extent of ischemic damage to the heart and heart tissue caused by metabolic and ionic abnormalities and disturbances. The current method will thus not prevent development of thrombi, atheromatous plaque, cholesterol or lipid deposits leading to ischemia and myocardial infarction.

The method of the current invention prevents or limits damage of the heart which would otherwise develop as a consequence of the ischemic insult. In its prophylactic mode the invention is utilized before the ischemia or before the metabolic and ionic abnormalities develop occurs but such prophylactic use will not prevent the ischemia to develop, it will only prevent or limit the extent of the damage and injury of the heart due to metabolic and ionic abnormalities developed during, following or associated with ischemia.

Myocardial ischemia usually develops as a result of a coronary artery disease such as occlusion of coronary artery due to sudden insufficiency of arterial or venous blood supply due to emboli, thrombi, or vascular torsion or due to a sudden increase in blood pressure. Any of these events can lead to ischemic insult such as myocardial ischemia where there is an inadequate circulation of blood to the myocardium resulting in a lack of oxygenated blood supply to the myocytes leading to a development of a necrotic area and damaged heart tissue. However, metabolic and ionic abnormalities may appear even without myocardial ischemia and infarction and may lead to impairment of the cardiac function.

The previously described methods concerned solely the prevention of the development of ischemia or myocardial infarction. The ischemia and myocardial infarction are mostly caused by the extraneous causes and by extracellular deposits as described above and, therefore, their prevention may be achieved by any method and/or compound which will prevent development and deposit of atheromatous plaque or thrombi by providing lipid or cholesterol lowering agents, by administering the antithrombotic, anticoagulation agents or antihypertensive agents so that the ischemia will not occur.

To the contrary, the current invention concerns decreasing and limiting the damage caused by ischemia or myocardial infarction but not the prevention of the ischemia per se. The damage and injury to the heart and heart tissue following or developing as a consequence of ischemia occurs on the intracellular level and leads to and causes a disturbance of normal cellular homeostasis of myocardial cells. Insufficient blood flow to the cardiac muscle depresses metabolism for three different reasons: lack of oxygen, excess of carbon dioxide and lack of sufficient nutrients. Due to the lack of oxygen, ionic abnormalities at the myocyte level, such as alterations in ion transport and ion regulation in myocytes, as well as changes in availability of high energy phosphates appear to be developing, later due to a switch from aerobic to anaerobic metabolism. For example, calcium overload resulting in decreasing contractile function which is connected to disturbed Na$^+$, K$^+$-ATPase activity, has been observed during and following ischemia. Consequently, the observed abnormalities in Na$^+$, K$^+$ and Ca$^{2+}$ ion regulation in normal and diabetic hearts may be important in determining the heart tissue response to ischemia.

The changes in intracellular conditions following the ischemic insult were studied in treated or untreated normal control and diabetic rat hearts under conditions of normal perfusion, global (zero-flow) ischemia, low-flow ischemia, and reperfusion and surprisingly it was found that the extent of the intracellular damage to the myocytes caused by the ischemic insult can be decreased, limited or prevented when the subject is treated with compounds able to change NADH/NAD$^+$ ratio and to stimulate glycolysis to increase production of ATP or with compounds which inhibit sodium-potassium-chloride cotransport.

Studies were performed on normal as well as on diabetic hearts because of the observed severity of the diabetic subjects response to the ischemic insult, including abnormalities that have been found in intracellular sodium and calcium in myocytes, sarcolemmal vesicles, and aorta from diabetic animals. Abnormalities in the sarcoplasmic reticular calcium pump and in the sarcolemmal ATP-dependent calcium transporter have been shown to have a significant effect on myocardial contractility and relaxation in diabetic subjects. Elevation in intracellular Na$^+$ levels observed in diabetic hearts were found to be primarily due to a reduced activity of Na$^+$, K$^+$-ATPase. Since this enzyme indirectly regulates intracellular calcium levels through its modulation of intracellular [Na$^+$]$_i$, the decrease in activity of Na$^+$, K$^+$-ATPase was expected to cause increases in intracellular $Na^+$ and $Ca^{2+}$. This was supported by data showing that in quiescent myocytes from diabetic hearts, cytosolic calcium levels are 30% higher than in controls (*Mol. Cell Biochem.*, 107:1 (1991)).

Function of both the sodium pump and the calcium transporters is dependent on ATP. Limited availability of high energy phosphate (ATP) during and after the ischemic insult thus may play an important role in the depressed cardiac function.

Prevention of development of metabolic and ionic abnormalities leading to heart and the heart tissue damage associated and/or resulting from ischemic insult according to the invention is based on preventing or limiting occurrence of these metabolic and ionic intracellular events by providing compounds which affect intracellular metabolism.

A. Inhibitors of Sodium-Potassium-Chloride Cotransport

Metabolic and ionic abnormalities observed during, following and associated with ischemia lead to a larger or smaller impairment of cardiac function. Their prevention or limitation of their extent is of utmost importance from the point of the survival of the individual who develops or is at risk of developing ischemia.

It has now been surprisingly found that compounds which inhibit cotransport of sodium-potassium-chloride through the myocyte wall are able to limit the extent of these metabolic and ionic abnormalities. These compounds are generally known as high ceiling diuretics. The most representative of these compounds are furosemide, piretanide, benzmetadine, bumetanide and toresamide and pharmaceutically acceptable salts and esters thereof.

I. Intracellular Abnormalities in Normal and Diabetic Heart Following the Ischemic Insult To determine whether intracellular abnormalities develop in normal and diabetic hearts, series of studies were performed. Specific studies were performed to determine whether altered intracellular sodium and calcium concentrations impair cardiac function in normal and diabetic hearts, whether interventions that limit an increase in intracellular sodium during ischemia in normal and diabetic hearts improve functional and metabolic recovery and limit infarct size upon reperfusion, whether interventions that lower intracellular sodium reduce ATP utilization and thereby $H^+$ generation during ischemia, and whether modulation of intracellular sodium regulates cytosolic free calcium levels in the hearts.

One of the major adverse complications of diabetes is the development of a diabetic cardiomyopathy characterized by defects in both diastolic and systolic function accompanied by an abnormal cation handling, primarily of sodium and calcium. The diabetic model was thus very suitable for measurement of the damage to the heart following the ischemic insult. To study the ionic basis of diabetic cardiomyopathy, the nuclear magnetic resonance spectroscopy (NMR) was utilized to measure high energy phosphates, intracellular pH, intracellular sodium and calcium, as well as other standard biochemical parameters.

Intracellular sodium, and calcium concentrations along with simultaneous measurements of end diastolic pressure (EDP), left ventricular developed pressure (LVDP), and heart rate in both diabetic and non-diabetic hearts were measured.

1. Altered Intracellular Sodium and Calcium Concentrations Impair Cardiac Function in the Heart To determine whether altered intracellular sodium and calcium concentrations impair cardiac function in diabetic and normal hearts, intracellular sodium and calcium concentrations were measured under normal perfusion conditions in diabetic and non-diabetic control hearts using NMR spectroscopy.

Sodium and calcium concentrations at steady state were obtained on both diabetic and non-diabetic rat hearts. Functional parameters such as end diastolic pressure (EDP) and left ventricular developed pressure (LVDP) were simultaneously monitored during the NMR experiments in groups of 9–12 diabetic BioBred (BB/W) rats and non-diabetic rats. Intracellular sodium and calcium were also measured in diabetic hearts of BB/W rats and non-diabetic rats during the following interventions: (a) inhibition of the $Na^+$-$K^+$-$2Cl^-$ cotransporter with bumetanide, and (b) inhibition of the cotransporter stimulation of the sodium pump with 8 mM $K^+$ along with functional parameters.

Isolated rat heart model is described in greater detail in Example 2. Briefly, diabetic and non-diabetic rat hearts were perfused in phosphate free Krebs-Henseleit buffer at 37° C. for 10 minutes before desired interventions were applied. The hearts were subjected to specific interventions such as inhibition of $Na^+$-$K^{+-}2Cl^-$ cotransporter, as described above, for 10 minutes before global ischemia was started. After 20 minutes of global ischemia, reperfusion with Krebs-Henseleit buffer was maintained for 60 minutes, a period of time sufficient to allow collection of the effluent for lactate and creatine kinase release. All reperfusion conditions were identical with regard to glucose substrate, and regulation of flow, in order to limit the effects of different reperfusion conditions.

This model allowed greater control of several variables, such as substrate and drugs and more complex measurements of metabolic events and consequently, allowed investigation of metabolic events under controlled conditions without potentially confounding effects of hormonal and neurologic influences.

Three groups of hearts studied included non-diabetic control, diabetics, and diabetics treated with bumetanide. Bumetanide is a representative inhibitor of $Na^+$-$K^+$-$2Cl^-$ cotransporter.

Results are shown in Table 1. Table 1 illustrates functional changes in heart rate, EDP, and LVDP in diabetic and non-diabetic rat hearts as well as the level of blood glucose. The measured values were determined at the beginning of ischemia (a), at the end of ischemia (b) and at the end of reperfusion (c).

TABLE 1

Functional Changes in Heart Rate, EDP, and LVDP in Diabetic and Non-diabetic Rat Hearts

| Heart | Blood Glucose (mg/dL) | EDP (cm $H_2O$) | LVDP (cm $H_2O$) | Heart Rate (bpm) |
|---|---|---|---|---|
| Non-Diabetic Control (C) | 92 ± 8 | (a) 10 ± 2<br>(b) 52 ± 3<br>(c) 36 ± 4 | (a) 108 ± 11<br><br>(c) 18 ± 5 | (a) 286 ± 12<br><br>(c) NR |
| Diabetic Control (DC) | 356 ± 21 | (a) 12 ± 3<br>(b) 63 ± 9<br>(c) 49 ± 11 | (a) 99 ± 8<br><br>(c) 21 ± 3 | (a) 198 ± 17<br><br>(c) NR |
| Diabetic + Bumetanide (DB) | 308 ± 32 | (a) 16 ± 2<br>(b) 35 ± 6<br>(c) 18 ± 4 | (a) 96 ± 12<br><br>(c) 66 ± 7 | (a) 180 ± 21<br><br>(c) 105 ± 27 |

NR = no recovery

As seen from Table 1, end developed pressure (EDP) in all three groups C, DC and DB was about 10–16 cm $H_2O$ at the beginning of the ischemia. At the end of ischemia, the end diastolic pressure (EDP) rose in untreated groups to about 52–63 cm $H_2O$, while in bumetanide treated diabetic group it rose only to about 35 cm $H_2O$. At the end of reperfusion, the EDP in diabetic treated group (DB) was close to that observed at the beginning of ischemia, while in untreated groups, this EDP was still 3–4 time higher. Results obtained with regard to the left ventricular developed pressure confirm the previous finding. In controls (DC and C) the LVDP was about 5 times lower at the end of reperfusion than at the beginning of ischemia. In DB group, the LVDP was also decreased, but only by about one third. Concerning the heart rate, there was no recovery in untreated groups. In treated DB group the heart rate was up to more than 50% of the preischemic heart rate. This correlates well with finding of LVDP in this group. These findings clearly confirm that intracellular ions are involved in post-ischemic damage to the heart tissue and that compounds which can control the ion transport can also ameliorate the heart tissue damage observed after ischemia.

In addition to functional recovery, creatine kinase (CK) release as a marker of cell necrosis was also measured. Results of these studies have demonstrated that creatine kinase release peaks at approximately 30 minutes of reperfusion; non-diabetic control hearts release an average of 756+54 units/gram/dry weigh (gdw) and diabetic hearts release 432+27 units/gdw of creatine kinase.

Importantly, bumetanide treated diabetic hearts under similar conditions had CK release of only 126+39 units/gdw.

Data obtained during these studies indicated that the studied interventions lowered intracellular sodium under baseline conditions with associated functional improvement, such as lowered EDP.

The diabetic hearts exhibited a lower heart rate than non-diabetic controls. Diabetic rat hearts perfused with 5 $\mu$M bumetanide had a markedly improved functional recovery. Since bumetanide blocks the inward flux of sodium via the cotransporter, thereby reducing intracellular sodium accumulation, these data show that inhibition of the cotransporter enhances functional recovery upon reperfusion after an episode of global ischemia in diabetics.

Increases in EDP during ischemia were higher in non-diabetic and diabetic controls than diabetics treated with bumetanide. LVDP recovery was significant in diabetic hearts treated with bumetanide, while others had poor recovery after ischemia. Bumetanide treated diabetic hearts also exhibited a return towards normal heart rate after ischemia and reperfusion.

2. Lowering Intracellular Sodium in the Heart Prior to Ischemia Improves Functional and Metabolic Recovery upon Reperfusion and Limits Infarct Size Studies, as outlined above, have clearly shown that the intracellular ion imbalance is involved in the post-ischemic damage of the heart tissue and that the treatment with the cotransporter inhibitor bumetanide, which blocks the inward influx of sodium into myocytes, is able to restore substantially the normal heart function in treated hearts.

The role of different sodium transport pathways (other than sodium pump) in the regulation of intracellular sodium in diabetic hearts was studied using $^{23}$Na NMR and concentrations of intracellular sodium in non-diabetic control and diabetic perfused rat hearts during global ischemia and reperfusion were determined. Intracellular sodium was measured in diabetic rat hearts subjected to a) sodium pump stimulation with 8 mM K$^+$, b) inhibition of the Na$^+$-K$^+$-2Cl$^-$ cotransporter with 5 $\mu$M bumetanide, and c) combined sodium pump stimulation and inhibition of the Na$^+$-K$^+$-2Cl$^-$ cotransporter. Hearts were subjected to these interventions for 10 minutes prior to 20 minutes of global ischemia followed by reperfusion in normal Krebs-Henseleit buffer for 60 minutes.

$^{23}$Na NMR spectra were collected every 5 minutes during the entire protocol. Functional parameters were compared for each intervention before, during, and after ischemia. The extent of ischemic injury was measured by total CK release following reperfusion.

Results supporting relationship between interventions that alter [Na$^+$]$_i$ and ATP utilization and pH generation during ischemia in normal and diabetic rat hearts are seen in FIG. 1.

FIG. 1 displays ATP utilization during ischemia in non-diabetic, diabetic, and bumetanide treated diabetic rat hearts. FIG. 1 shows ATP (as a fraction of control) in non-diabetic control [■], diabetic [♦], bumetanide [□], bumetanide +8 mM K$^+$ [●], and 8 mM K$^+$ [▲] perfused hearts. The time points shown are obtained during global ischemia.

The diabetic hearts appear to utilize less ATP initially in the first 5 minutes of ischemia than non-diabetic hearts. Inhibition of the Na$^+$-K$^+$-2Cl$^-$ cotransporter with 5 $\mu$M bumetanide prior to ischemia exhibited maximum conservation in ATP during ischemia compared to all other groups. Stimulation of the sodium pump in diabetic hearts using 8 mM K$^+$ coupled with inhibition of cotransporter had marginally better conservation of ATP than untreated diabetic hearts during ischemia. These data show that sodium influx via the cotransporter is increased in diabetics and that its inhibition lowers intracellular sodium, lowering the workload on the sodium pump, thereby lowering ATP requirements of the sodium pump.

Figure 2:
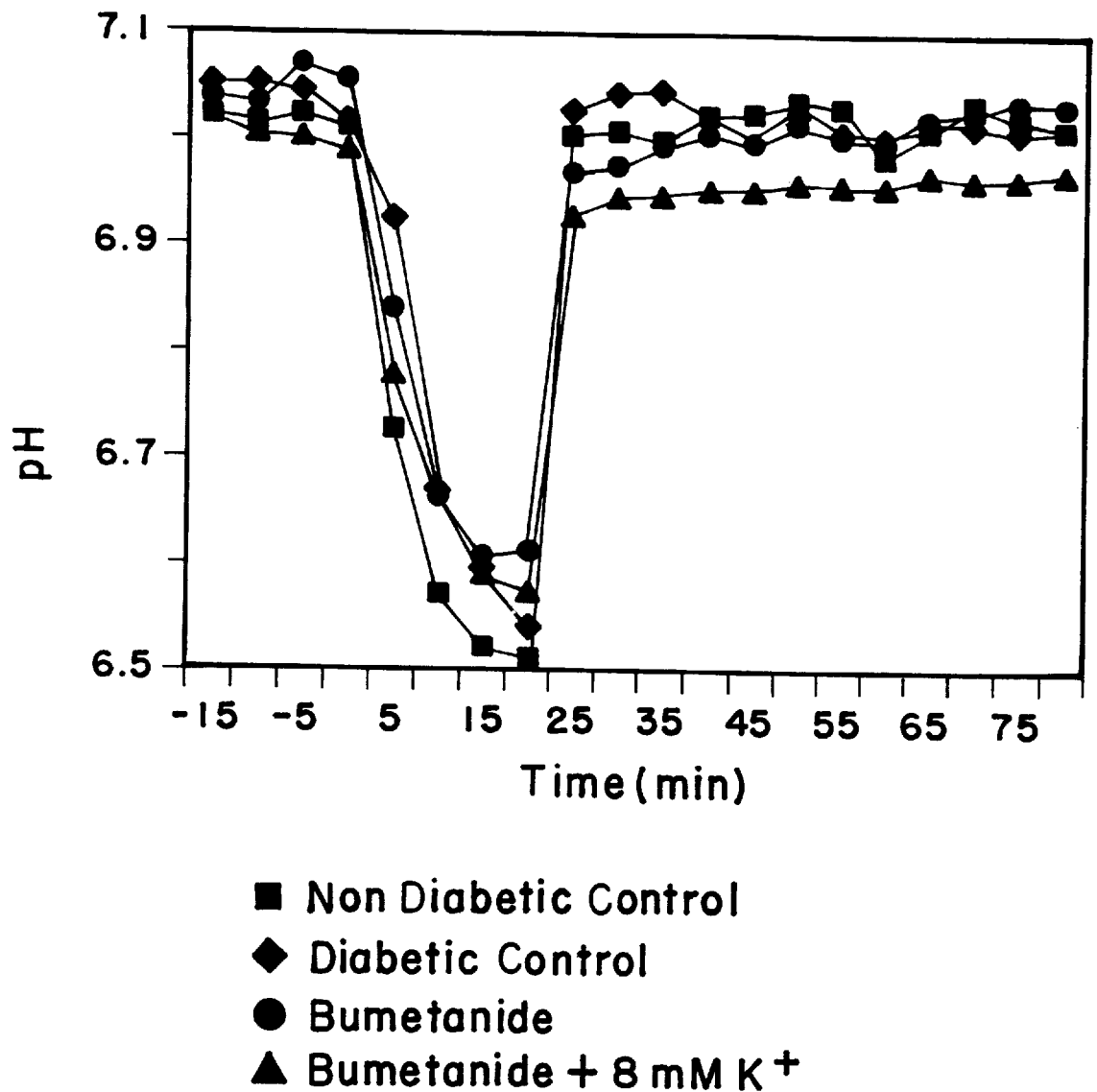
FIG. 2 shows intracellular pH in perfused hearts from non-diabetic controls, diabetic and diabetic treated with bumetanide and diabetic treated with bumetanide plus 8 mM K$^+$.

FIG. 2 shows changes in intracellular pH in perfused hearts from non-diabetic control, diabetic, diabetic treated with bumetanide, and diabetic treated with bumetanide +8 mM K$^+$. Intracellular pH in perfused hearts from non-diabetic control [■], diabetic [♦], diabetic treated with bumetanide [●], diabetic treated with bumetanide +8 mM K$^+$ [▲]. The time prior to ischemia is denoted in negative values. Duration of ischemia was for 20 minutes.

The rate of acidification seen in FIG. 2 was slower in diabetic hearts during ischemia than non-diabetic controls. During the first 10 minutes of ischemia, a statistically significant difference in pH values were observed between diabetics and non-diabetic controls. However, at the end of 20 minutes of ischemia, pH was not significantly lowered between the two groups, suggesting a slower rate of proton production in diabetics. Upon reperfusion, pH recover rapidly in non-diabetic controls while in diabetics it was more gradual.

Diabetic hearts treated with bumetanide or bumetanide with 8 mM K$^+$ became less acidic during ischemia than non-diabetic controls. They also exhibited rapid pH recovery on reperfusion. At the end of 20 minutes of ischemia pH values in bumetanide or bumetanide with 8 mM K$^+$ treated diabetic hearts were different than non-diabetic controls. The changes in pH follow ATP utilization in all the groups studied here. These data show that ATP is the prime source of proton generation.

These studies show that sodium accumulation is the primary event responsible for defective calcium homeostasis in diabetic hearts and impairment of sodium transport pathway(s) is the responsible for sodium accumulation causing calcium overload during and following ischemia in diabetic hearts.

Interventions that lower intracellular sodium in diabetic hearts prior to the onset of ischemia, lowered the rise in intracellular sodium and calcium during ischemia, enabling the hearts to recover functionally and metabolically upon reperfusion.

3. Lowering Intracellular Sodium Reduces ATP Utilization and H$^+$ Generation During Ischemia ATP utilization during global ischemia is primarily dependent on the activity of ATP requiring pumps, hearts with increased activity of $Na^+$, $K^+$-ATPase thus have a rapid utilization of ATP. Therefore, inhibition of the $Na^+$-$K^+$-$2Cl^-$ cotransporter was expected to reduce the rate of ATP utilization during global ischemia and improve recovery. This was tested by measuring the rate of ATP depletion and pH production in diabetic hearts during global ischemia under conditions of sodium pump stimulation and inhibition of $Na^+$-$K^+$-$2Cl^-$ cotransporter.

Using $^{31}p$ NMR spectroscopy, changes in the rate of ATP utilization and pH production in diabetic hearts subjected to ischemic insult were measured. ATP, phosphocreatine (PCr) expressed as fraction of control, and pH were measured in hearts before ischemic intervention, after intervention, during ischemia, and during reperfusion. Lactate and creatine kinase measurements were made in the effluent collected during NMR experiments prior to ischemia and during reperfusion for all hearts. In addition, ATP concentrations were measured using biochemical assays for non-diabetic control and diabetic hearts under normal perfusion conditions. Using the values of ATP obtained biochemically, the NMR obtained ATP areas were converted to concentrations.

To measure changes in intracellular sodium $[Na^+]_i$, the shift reagent Tm-DOTP$^{-5}$ was employed to examine the changes in intracellular sodium $[Na^+]_i$ during ischemia and reperfusion in diabetic and non-diabetic hearts (n=2 in each group).

Figure 3:
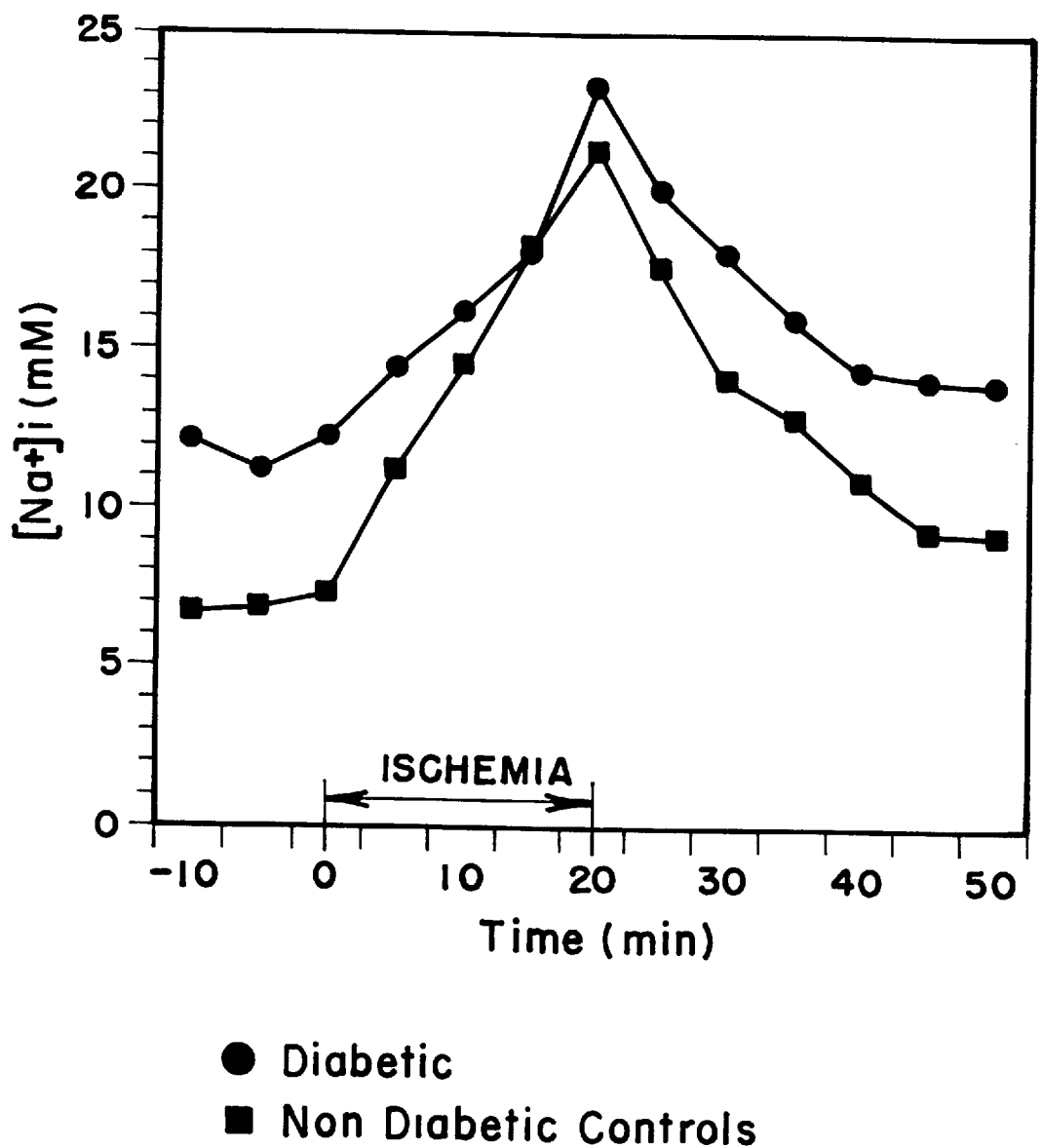
FIG. 3 shows intracellular sodium concentrations in diabetic and non-diabetic controls hearts during ischemia and reperfusion.

Results supporting altered sodium regulation fluxes in diabetic hearts are seen in FIG. 3. FIG. 3 shows intracellular sodium concentrations in diabetic (●) and non-diabetic control hearts (0) during ischemia and reperfusion.

As shown in FIG. 3, diabetic hearts had higher baseline $[Na^+]_i$ than that of the control hearts. The 20 minute ischemic episode resulted in equivalent increases in $[Na^+]_i$ in both groups at the end of ischemia. However, the rise in $[Na^+]_i$ (0–5 mins) was lower in the diabetic hearts than nondiabetic controls. These data are consistent with inhibition of the $Na^+$-$H^+$ exchanger. Therefore, the slower increase in $[Na^+]_i$ early during ischemia reflects the net activity of the $Na^+$-$H^+$ exchanger and the $Na^+$-$K^+$-$2Cl^-$ cotransporter. While it has been believed that high levels of $[Na]_i$ observed in diabetics are due to inhibition of the $Na^+$-$K^+$ pump, the current results indicate that increased activity of the $Na^+$-$K^+$-$2Cl^-$ cotransporter is important in the higher level of intracellular sodium in diabetic hearts. Since intracellular sodium concentration regulates calcium flux via $Na^+$-$Ca^{2+}$ exchanger, the inability of diabetic heart to maintain low intracellular sodium may in part cause calcium accumulation.

Data from $^{31}P$ NMR studies demonstrated that inhibition of the $Na^+$-$K^+$-$2Cl^-$ cotransporter in diabetic hearts prior to ischemia, resulted in lower fall in pH during ischemia and in a significant functional and metabolic recovery on reperfusion. The inhibition of the $Na^+$-$K^+$-$2Cl^-$ cotransporter limited ischemic injury and enabled functional and metabolic recovery in diabetic hearts.

The performed studies determined the relationship between ATP utilization and pH production during ischemia in diabetic hearts subjected to interventions that alter intracellular sodium. The rate of ATP utilization, and hence pH production, during ischemia is reduced by interventions that lower intracellular sodium in diabetic hearts.

Studied interventions which lowered intracellular sodium accumulation exhibited reduced ATP utilization, reduced pH during ischemia, lowered lactate afflux and lower CK release upon reperfusion. Bumetanide as representative of $Na^+$-$K^+$-$2Cl^-$ cotransporter inhibitor was responsible for normalizing functional and metabolic recovery after ischemic insult.

4. Modulation of Intracellular Sodium Regulates Cytosolic Free Calcium Levels in the Heart Changes in intracellular calcium $[Ca^{2+}]_i$ were also followed as the end result of ischemic damage seems due, in part, to calcium overload during ischemia and reperfusion. Calcium homeostasis has also been shown to be impaired in diabetics.

As it was unclear from the above studies, whether the altered calcium homeostasis in diabetic hearts is entirely due to impaired $Na^+$-$Ca^{2+}$ exchanger or due to other calcium regulatory mechanisms, intracellular sodium levels were altered and intracellular calcium levels in diabetic hearts were observed. These experiments enabled to establish the role of sodium towards altered calcium homeostasis in diabetic hearts.

Using 5F-BAPTA and $^{19}F$ NMR spectroscopy, intracellular calcium in perfused hearts was measured. Intracellular sodium levels and intracellular calcium levels in diabetic hearts were observed.

Figure 4:
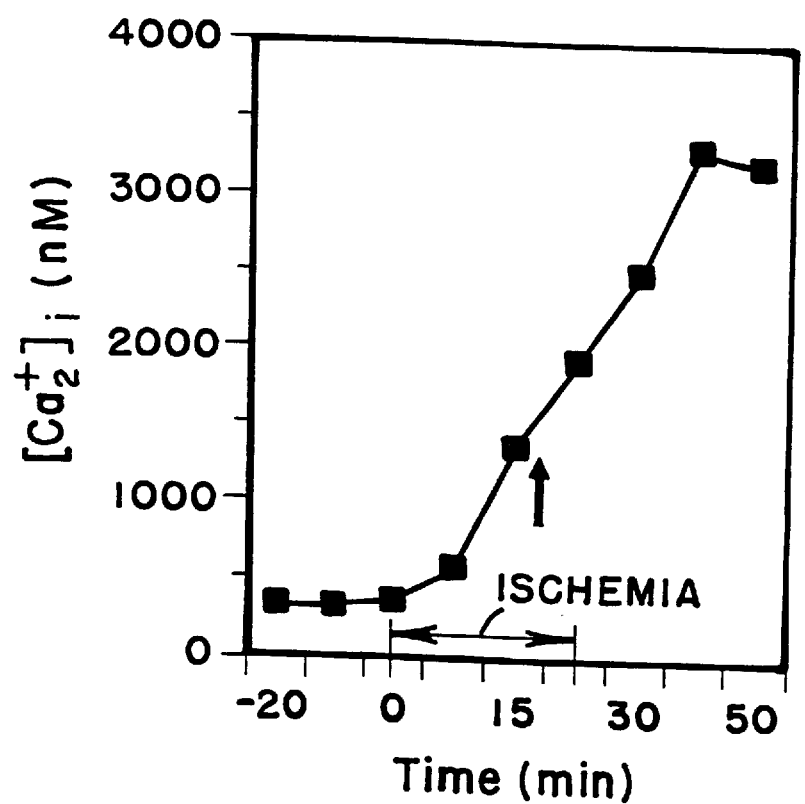
FIG. 4 shows intracellular calcium during normal, ischemic and reperfusion periods.

Data supporting changes in calcium flux during ischemia are seen in FIG. 4. FIG. 4 shows a concentration of intracellular calcium during normal, ischemic, and reperfusion periods. Negative time denotes perfusion prior to ischemia. Duration of global ischemia was for 20 minutes. Arrow indicates reperfusion.

Experiments performed using 5F-BAPTA and $^{19}F$ spectroscopy indicated that ischemia causes a rise in intracellular calcium $[Ca^{2+}]_i$ as seen in FIG. 4, in non-diabetic control hearts and that $[Ca^{2+}]_i$ continued to increase on reperfusion.

As also seen in FIG. 4, intracellular calcium continued to increase from the time of ischemia for the whole duration of the study up to about 40 minutes post ischemia. Only at the last ten minutes there was a slight decrease in intracellular calcium concentration. Since intracellular calcium is an important modulator of ischemic injury, reduction of intracellular calcium either during ischemia or reperfusion reduces cells injury.

B. Inhibitors od Aldose Reductase

As discussed above, metabolic and ionic abnormalities observed during, following and associated with ischemia lead to a larger or smaller impairment of cardiac function.

It has now been also surprisingly found that compounds which change ratio of NADH/NAD$^+$ are able to limit the extent of these metabolic and ionic intracellular abnormalities. The most representative of these compounds are generally known as aldose reductase inhibitors such as zopolrestat, zenorestat, epolrestat and tolrestat. Additionally, compounds such as nicotinic acid and methylene blue are useful in this respect.

I. Effect of Compounds Reducing NADH/NAD$^+$ Ratio and Extent of Post-Ischemic Insult Ischemic insult to the heart results in metabolic and ionic abnormalities and in damage of the heart tissue eventually leading to a cellular edema and myocardial necrosis.

High levels of glucose in many tissues lead to the accumulation of sorbitol via the polyol pathway. In this pathway, a family of aldo-keto reductase enzymes utilize hexoses as a substrate for reduction to their respective sugar alcohols. Accumulation of sorbitol is due to a reaction catalyzed by the enzyme aldose reductase, coupled with the oxidation of NADPH to NADP$^+$. Increased production of sorbitol seems to be connected with of numerous diabetic complications.

It has now been found that compounds which affect this reaction, as described in Scheme 1, particularly compounds which reduce NADH/NAD$^+$ ratio also affect the tolerance of the heart to metabolic and ionic abnormalities arising from global ischemia, and that compounds which inhibit this reaction assert certain protective effects on the heart tissue. As shown above, this protective effect happens on the cellular and intracellular level and may be due to alteration of sodium-potassium pump, shift in glucose utilization from the sorbitol (polyol) pathway to glycolysis, and enhanced glycolytic and TCA cycle flux.

As seen in Scheme 1 glucose is reduced to sorbitol by aldose reductase and sorbitol then is oxidized by sorbitol dehydrogenase to fructose. The flux through aldose reductase requires NADH, while sorbitol dehydrogenase requires NAD$^+$.

SCHEME 1

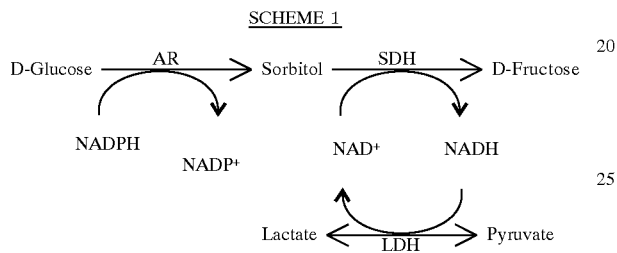

Scheme 1 illustrates the impact of the sorbitol pathway on the cytosolic ratios of lactate/pyruvate (L/P) and free NADH/NAD$^+$. In the first step of the pathway, glucose is reduced to sorbitol by aldose reductase (AR) coupled with the oxidation of NADPH to NADP$^+$. In the second step sorbitol is oxidized to fructose by sorbitol dehydrogenase (SDH) coupled with reduction of NAD$^+$ to NADH. Since the lactate dehydrogenase (LDH) reaction is reversible, a change in cytosolic ratio of NADH/NAD$^+$ is reflected by a change in the ratio of lactate/pyruvate (LP). The increased ratio of free NADH/NAD$^+$ is important in the observed metabolic and ionic abnormalities.

Several abnormalities in ion regulation in diabetic hearts have been shown in studies involving isolated hearts described above from diabetic animals. These abnormalities include increases in intracellular sodium and calcium under baseline conditions, with the elevation in intracellular Na$^+$ levels observed in diabetic hearts primarily due to reduced activity of Na$^+$, K$^+$-ATPase.

SCHEME 2

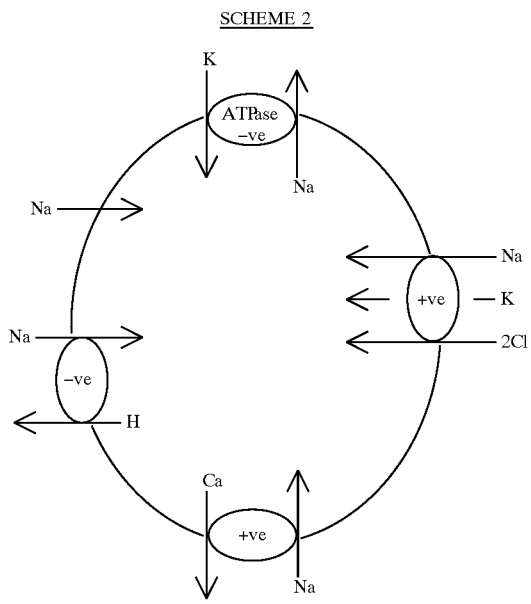

Scheme 2 illustrates major sodium transport pathways operational under baseline conditions in a perfused heart.

(+ve) sign denotes that this pathway has higher activity in diabetic hearts, (–ve) sign denotes impaired activity in diabetics.

The alterations in cardiac sodium and calcium transporters in diabetics present a natural model of pathophysiology that was helpful in understanding the regulation of these ions during ischemia and reperfusion. Functional measurement of changes in sodium and calcium in diabetic hearts, both with and without interventions that alter their response to ischemia, provides evidence that limiting the rise in sodium and calcium during ischemia and reperfusion is cardioprotective.

Effect of compounds reducing NADH/NAD$^+$, such as for example, aldose reductase inhibitors, on ion regulation was investigated in view of the previously obtained results. Impaired Na$^+$, K$^+$-ATPase activity depends on the sorbitol (polyol) pathway, in which high concentrations of glucose lead to the accumulation of sorbitol through aldose reductase catalyzed reaction (Scheme 1). *Diabetes Care*, 8:290 (1988) suggested that sorbitol interferes with myo-inositol accumulation in tissues. As shown in Scheme 3, myo-inositol is directly responsible for regulating phosphatidyl inositol (Ip3) levels in the heart, with Ip3 a second messenger involved in calcium mobilization in sarcoplasmic reticulum.

SCHEME 3

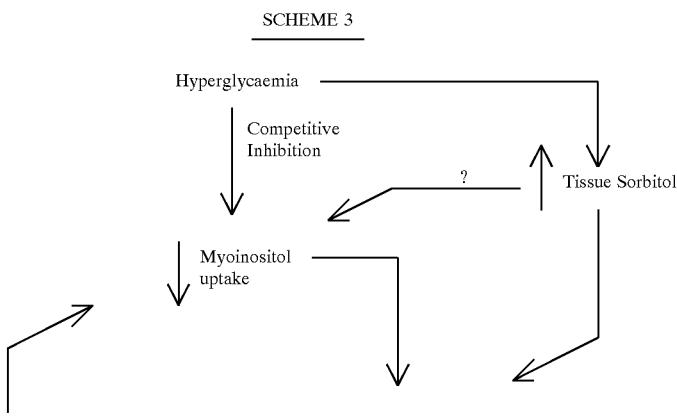

-continued
SCHEME 3

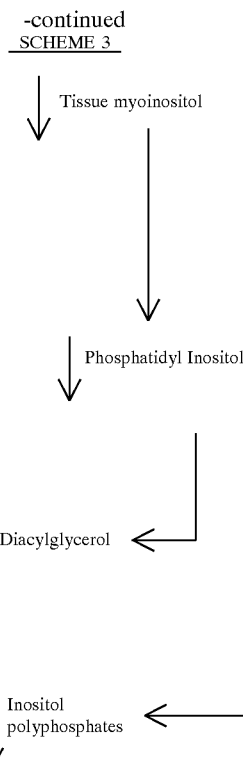

Scheme 3 illustrates mechanism by which sorbitol accumulation can potentially lower the activity of Na$^+$, K$^+$-ATPase in diabetic heart tissue.

The dependence of Na$^+$, K$^+$-ATPase on glycolysis has been previously established under both normoxic and hypoxic conditions. *J. Clin. Invest.*, 75:436 (1985) described that inhibition of glycolysis under normoxic conditions results in significant impairment of the Na$^+$, K$^+$-ATPase, with a mechanism for the action of glucose suggested by transient glycation of Na$^+$, K$^+$-ATPase.

During the development of the current invention, the findings that diabetes increases both the incidence of cardiovascular disease and complications of myocardial infarction and heart failure were followed. Studies described above, using animal diabetes models, have demonstrated that the metabolic alterations occurring at the myocyte level may contribute to the severity of ischemic injury in diabetic hearts, and that the increased metabolism of glucose via the sorbitol pathway may be involved. Obtained results indicate that inhibition of aldose reductase, a key regulatory enzyme in the sorbitol pathway limits metabolic and ionic abnormalities, reduces infarct size and improves functional and metabolic recovery after zero-flow ischemia and low-flow ischemia (~10% of baseline flow) in perfused diabetic and normal non-diabetic hearts. The protective effect of aldose reductase inhibition results from increase glycolysis and increased activity of Na$^+$, K$^+$-ATPase in diabetic hearts. This was tested by first measuring changes in (a) the rate of glycolysis and (b) the activity of the Na$^+$, K$^+$-ATPase in untreated and aldose reductase inhibited diabetic hearts. Aldose reductase inhibition protects diabetic hearts during zero-flow and low-flow ischemia.

Aldose reductase inhibition lowers the cytosolic NADH/NAD$^+$ ratio, resulting in increased glycolysis under normoxic conditions in diabetic hearts.

Aldose reductase inhibition was achieved using as the representative the aldose reductase inhibitor, zopolrestat. The ratio of lactate/pyruvate, which is an indicator of the cytosolic redox state NADH/NAD$^+$, was measured in perfused diabetic hearts in both the presence and absence of zopolrestat. Changes in glycolysis due to aldose reductase inhibition were monitored using $^{13}$C NMR by perfusing hearts with $^{13}$C labeled-C-1 glucose and observing changes in the C-3 labeled lactate areas as a function of time. The data obtained from diabetic hearts were compared with those obtained from non-diabetic control hearts.

1. Aldose reductase inhibition lowers the cytosolic NADH/NAD$^+$ ratio

Aldose reductase inhibition lowers the cytosolic NADH/NAD$^+$ ratio, resulting in increased glycolysis under normoxic conditions in diabetic hearts.

Lactate/pyruvate ratios were determined to assess the influence of aldose reductase inhibition on the cytosolic redox state. The rate of change in lactate concentrations, as well as those of glycolytic intermediates, were determined in order to examine glycolytic fluxes.

Initial studies were performed to determine the minimum effective dose of zopolrestat without any significant effect on hemodynamics of the heart. Exact protocols are described in examples.

During perfusion of diabetic hearts with zopolrestat at concentrations of 5 $\mu$M, a significant lowering of left ventricular developed pressure (LVDP) was observed. Diabetic hearts, perfused with 1 $\mu$M zopolrestat for 10 minutes did not show the hemodynamic changes found at 5 $\mu$M. Based on those results, 1 $\mu$M zopolrestat was found to be the optimal dose.

A link between the changes in NADH/NAD$^+$ and glycolysis was obtained by measuring the lactate/pyruvate (L/P) ratios in diabetic and zopolrestat treated diabetic hearts.

As shown in Scheme 1, the L/P ratio reflects the cytosolic ratio of NADH/NAD$^+$.

Lactate/pyruvate ratios were measured in freeze-clamped heart tissue extracts (n=3/group). Results are shown in Table 2.

Table 2 shows lactate/pyruvate ratios in diabetic untreated (DC), zopolrestat (1 μm) treated diabetic (DZ), and non-diabetic control (C) hearts.

TABLE 2

| Hearts | L/P ratio |
|--------|-----------|
| DC | 56.34 ± 6.58* |
| DZ | 9.26 ± 3.12 |
| C | 12.56 ± 2.17 |

*$p < 0.01$ vs DZ and C hearts

As shown in Table 2, the L/P ratios were significantly elevated in diabetic untreated (DC) hearts compared to control (C) hearts. Aldose reductase inhibition in treated diabetic hearts (DZ) lowered the L/P ratios to values similar to those observed in non-diabetic hearts.

2. Aldose Reductase Inhibition Improves Glycolysis in the Heart

In order to accurately determine glycolytic flux using $^{13}C$ NMR, incorporation of the label into hearts in the presence and absence of zopolrestat was followed. These hearts were freeze-clamped and the neutralized perchloric acid extracts was examined by 13C NMR. The $^{13}C$ NMR spectra of perfused hearts and their extracts were analyzed for the appearance of lactate (C3) and glutamate (C2, C3, C4) resonances, reflecting glycolytic flux and entry of substrates into the TCA cycle. Functional parameters such as end diastolic pressure, (EDP) and left ventricular developed pressure (LVDP), were monitored simultaneously during the NMR experiments.

Figure 5:
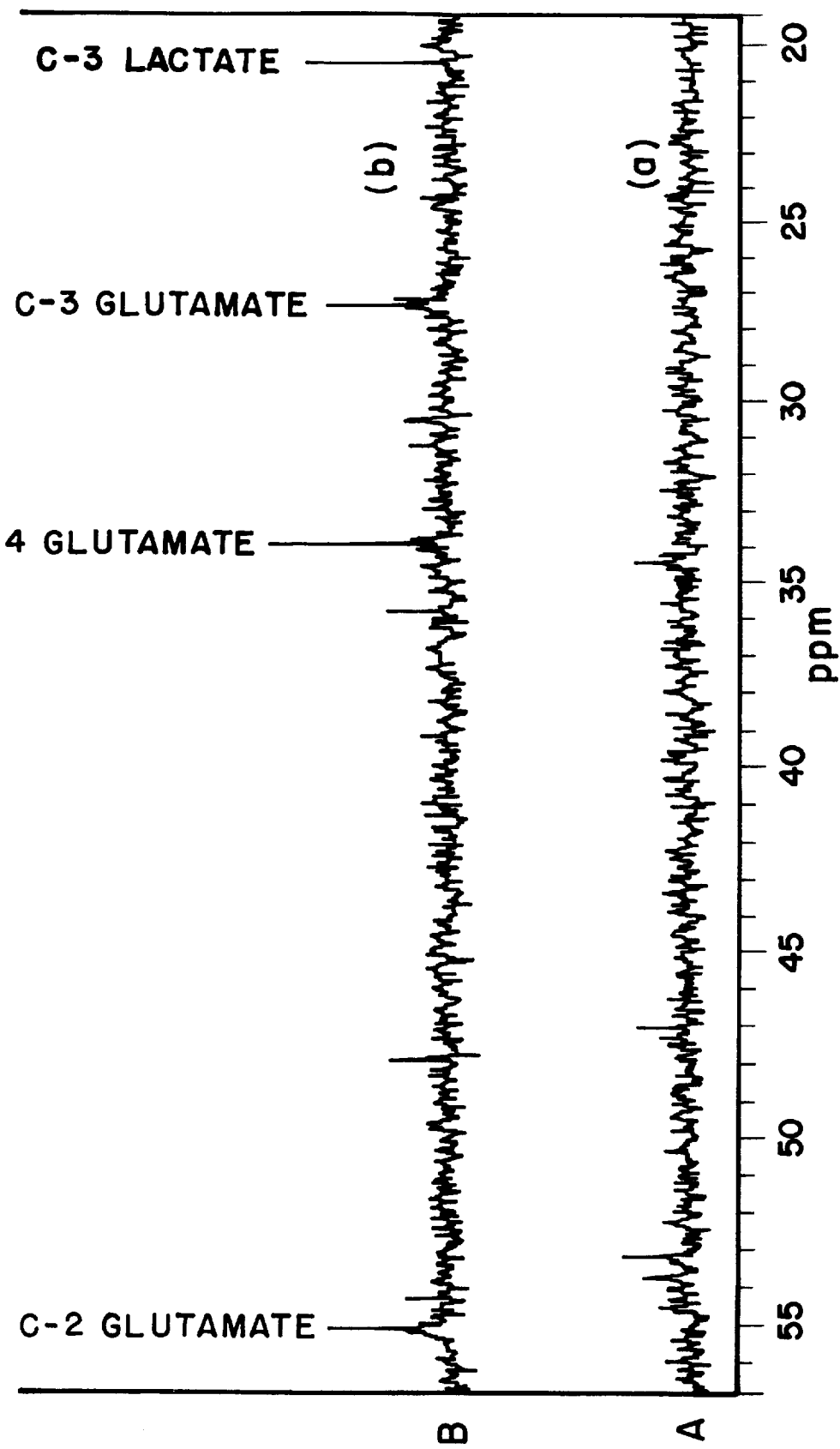
FIG. 5 depicts $^{13}$C NMR spectra of neutralized perchloric acid extracts from diabetic controls (FIG. 5A) and from zopolrestat (FIG. 5B) treated diabetic hearts.

Results are shown in FIG. 5. FIG. 5 shows $^{13}C$ NMR spectra of neutralized perchloric acid extracts from (a) diabetic control, and (b) diabetic hearts treated with aldose reductase inhibitor, zopolrestat. Both hearts were perfused with C-1 labelled $^{13}C$-glucose for 1 hour prior to freeze-clamping.

FIG. 5 displays the incorporation of $^{13}C$ label into lactate (observed at C-3) in diabetic hearts treated with zopolrestat. Glutamate is seen as C2, C3 and C4 resonances. The lactate labelling is consistent with metabolism of glucose through glycolysis. In contrast, untreated diabetic hearts did not incorporate the $1^3C$ label into lactate or glutamate, consistent with impairment in glucose uptake, glycolysis, and pyruvate dehydrogenase activity. These data show that treatment of diabetic heart with aldose reductase inhibitor, zopolrestat, increases glycolysis.

3. Aldose Reductase Inhibition Normalizes $Na^+$, $K^+$-ATPase Activity

Aldose reductase inhibition normalizes $Na^+$, $K^+$-ATPase activity in diabetic hearts. This increased $Na^+$, $K^+$-ATPase activity then limits the rise in intracellular sodium during ischemia and improves functional and metabolic recovery upon reperfusion.

Activity of $Na^+$, $K^+$-ATPase and changes in intracellular sodium in aldose reductase inhibited diabetic hearts and control hearts under conditions of zero-flow and low-flow ischemia were measured.

The activity of $Na^+$, $K^+$-ATPase in hearts from zopolrestat treated, untreated diabetic, and non-diabetic controls were measured using a biochemical assay under baseline and ischemic conditions. Intracellular sodium in diabetic rat hearts, treated with and without zopolrestat, was measured using $^{23}Na$ NMR. Spectra were obtained every 5 minutes during the ischemia and reperfusion protocol. Diabetic and zopolrestat treated diabetic hearts were subjected to (a) zero-flow ischemia for 20 minutes followed by 60 minutes of reperfusion; or (b) low-flow ischemia (90% reduction in flow rate) for 30 minutes and 30 minutes of reperfusion at normal flow rates (12.5 ml/min). Functional parameters of LVDP, EDP, and rate pressure product (RPP) were compared for each intervention before, during, and after zero-flow as well as after low-flow ischemia. The extent of ischemic injury in hearts subjected to zero-flow ischemia was assessed by measuring total creatine kinase (CK) release during 60 minutes reperfusion. In the case of low-flow experiments, a comparison of LVDP, EDP, and RPP under baseline, ischemic and reperfusion conditions were made to asses the ability of hearts to recover from ischemic insult.

Pre-ischemic $Na^+$, $K^+$-ATPase activity in diabetic hearts treated or untreated with the aldose reductase inhibitor, zopolrestat, were determined. $Na^+$, $K^+$-ATPase activity was obtained on freeze-clamped hearts using a standard biochemical assay. Continuous measurement of intracellular sodium was performed using shift reagent aided $^{23}Na$ NMR spectroscopy in perfused diabetic hearts during zero-flow ischemia, low-flow (10% of baseline flow) ischemia, and upon reperfusion.

Aldose reductase inhibition normalizes $Na^+$, $K^+$-ATPase activity, which then limits the rise in intracellular sodium during ischemia and reperfusion in diabetic hearts.

The $Na^+$, $K^+$-ATPase activity (expressed as nmoles of ADP/min/mg total protein) were 14.2±3.2 in non-diabetic, 3.9±1.2 in diabetics, and 12.6±2.9 (n=3 in each group) in zopolrestat treated diabetic hearts. Results are seen in Table 3.

TABLE 3

| Hearts | $Na^+$, $K^+$-ATPase activity (nmoles of ADP/min/mg total protein) |
|--------|-----------|
| C | 14.2 + 3.2 |
| D | 3.9 + 1.2 |
| DZ | 12.6 + 2.9 |

Aldose reductase inhibition normalizes $Na^+$, $K^+$-ATPase activity which then limits the rise in intracellular sodium during zero-flow ischemia and reperfusion. The shift reagent Tm-DOTP-$^{-5}$ was employed to examine the changes in intracellular sodium [$Na^+$]$_i$ during zero-flow ischemia and reperfusion in diabetic and zopolrestat treated diabetic hearts (n=3/group). Results are shown in FIG. 6.

Figure 6:
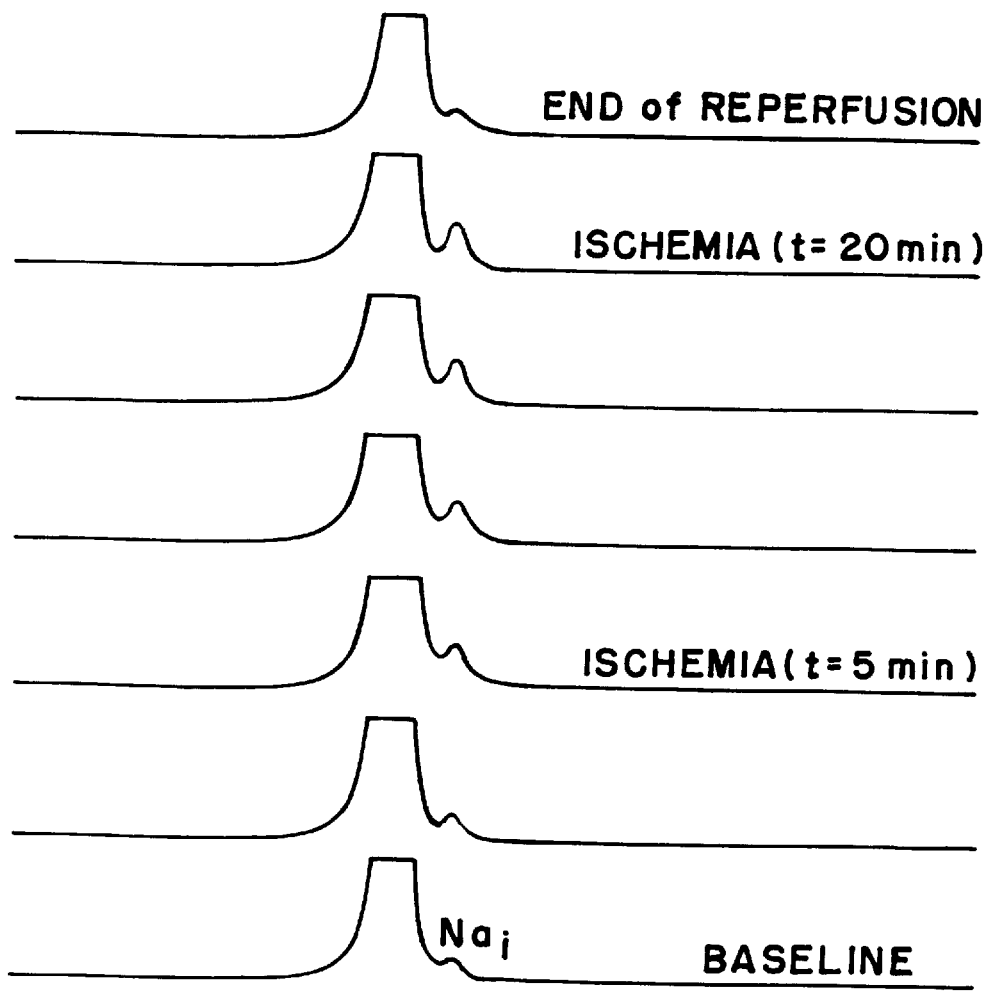
FIG. 6 is $^{23}$Na NMR spectra obtained in perfused diabetic control hearts under baseline, zero-flow ischemic and reperfusion conditions.

FIG. 6 shows typical $^{23}Na$ NMR spectra obtained using 3.5 mM Tm-DOTP-$^{-5}$, as the shift reagent, in perfused diabetic control (DC) hearts. The excellent resolution of intracellular sodium ($Na^+$)$_i$ is demonstrated under baseline, ischemic (zero-flow), and reperfusion conditions. Changes in intracellular sodium during baseline, zero-flow ischemia and under reperfusion conditions in diabetic controls and diabetic hearts treated with aldose reductase inhibitor zopolrestat are shown in FIG. 7.

Figure 7:
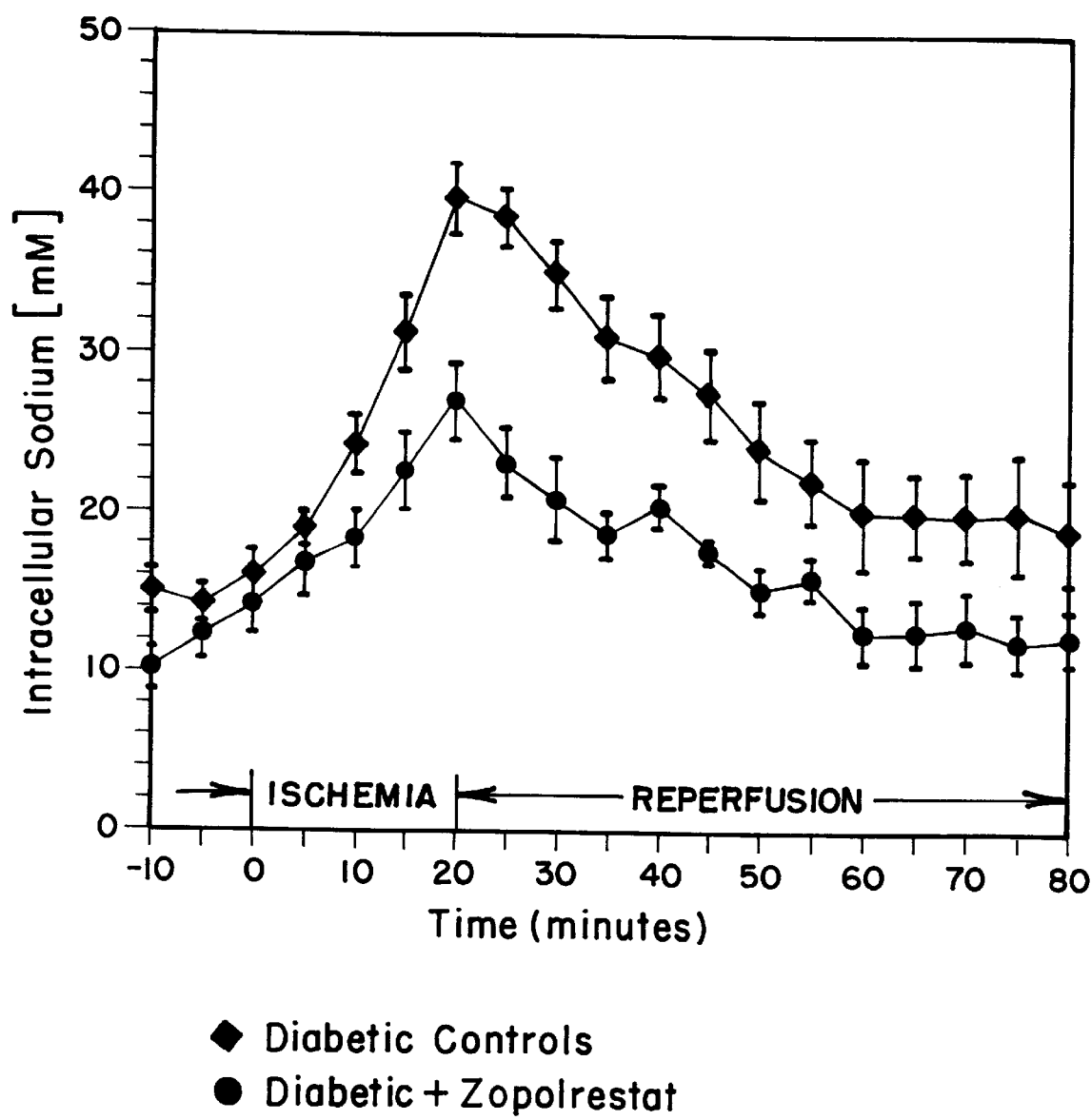
FIG. 7 is a graph showing changes in intracellular sodium in diabetic control and zopolrestat treated diabetic hearts during baseline, zero-flow ischemia and reperfusion conditions.

FIG. 7 shows a plot of changes in intracellular sodium (in mM) measured during baseline, zero-flow ischemia, and reperfusion conditions in diabetic control (DC) and zopolrestat treated diabetic (DZ) hearts. Hearts were subjected to 10 minutes of baseline perfusion, 20 minutes of zero-flow ischemia (ischemia started at time zero), and 60 minutes of reperfusion.

Plot of [$Na^+$]$_i$ obtained during zero-flow ischemia, as shown in FIG. 7, demonstrates that diabetic hearts had higher baseline [$Na^+$]$_i$ than did zopolrestat treated diabetic hearts. The 20 minute zero-flow ischemia resulted in a significantly smaller increase in [$Na^+$]$_i$ in zopolrestat treated diabetic hearts than in the untreated diabetic hearts. This smaller increase in $[Na^+]_i$ early during zero-flow ischemia seems to reflect the net activity of the $Na^+$-$H^+$ exchanger and the $Na^+$-$K^+$-$2Cl^-$ cotransporter. The higher baseline levels of $[Na^+]_i$ observed in diabetics are consistent with the reduced $Na^+$, $K^+$-ATPase activity measured above, although increased activity of the $Na^+$-$K^+2Cl^-$ cotransporter may also be an important mechanism contributing to the higher level of intracellular sodium in diabetic hearts. Therefore, the reduction in the rise of intracellular sodium in aldose reductase inhibited hearts may, in part, be due to the influence of zopolrestat on $Na^+$-$K^+$-$2Cl_-$ cotransporter activity.

4. Aldose Reductase Inhibition Conserves ATP During Ischemia and Normalizes pH Recovery on Reperfusion Because ATP utilization during ischemia is primarily dependent on the activity of ATP-requiring processes, diabetic hearts with normalized $Na^+$, $K^+$-ATPase activity were expected to exhibit rapid ATP utilization. However, the beneficial effect of normalized $Na^+$, $K^+$-ATPase activity in aldose reductase inhibited hearts is likely via effects on other ATP-requiring ion transporters (such as $Na^+$-$H^+$ exchanger and $Na^+$-$K^+$-$2Cl^-$ cotransporter) leading to overall reduction in ATP utilization. This was tested by measuring changes in ATP and pH during zero-flow and low-flow ischemia and reperfusion in zopolrestat treated and untreated perfused diabetic hearts using $^{31}P$ NMR and biochemical assays.

Using $^{31}P$ NMR spectroscopy, changes in ATP and pH in diabetic hearts perfused with and without zopolrestat were measured. ATP, PCr (expressed as fraction of baseline), and pH was measured in hearts before intervention, after intervention, during ischemia, and during reperfusion. The ischemic conditions were zero-flow and low-flow ischemia. Lactate and creatine kinase measurements were made on the effluent collected during NMR experiments, prior to ischemia, during low-flow ischemia, and during reperfusion (after zero-flow and low-flow ischemia) for all hearts. In addition, ATP concentrations were obtained using biochemical assays on zopolrestat treated and untreated diabetic hearts under normal perfusion conditions.

The interventions which lower intracellular sodium accumulation exhibited reduced ATP utilization, reduced acidosis during ischemia, lower lactate efflux and lower CK release upon reperfusion.

5. Zero-Flow Ischemia in Diabetic Hearts Functional Post-Ischemic Recovery

Functional post ischemic recovery after zero-flow ischemia confirmed that the hearts treated with aldose reductase inhibitor has much better function than those of non-diabetic and diabetic controls. Results are seen in Table 4.

Table 4 illustrates functional changes in heart rate, EDP, and LVDP in diabetic and non-diabetic rat hearts treated with zopolrestat.

TABLE 4

| Heart | EDP (cm $H_2$)) | LVDP (cm $H_2O$) | Heart Rate (bpm) |
| --- | --- | --- | --- |
| Non-diabetic control (C) | (b) 10 ± 2 | (b) 108 ± 11 | (b) 286 ± 12 |
|  | (i) 52 ± 3 |  |  |
|  | (r) 36 ± 4 | (r) 18 ± 5 | (r) 18 ± 9 |
| Diabetic control (DC) | (b) 12 ± 3 | (b) 99 ± 8 | (b) 198 ± 17 |
|  | (i) 63 ± 9 |  |  |
|  | (r) 49 ± 11 | (r) 21 ± 3 |  |
| Diabetic + zopolrestat (DZ) | (b) 16 ± 2 | (b) 108 ± 12 | (b) 180 ± 21 |
|  | (i) 45 ± 6 |  |  |
|  | (r) 18 ± 4 | (r) 66 ± 7 | (r) 105 ± 27 |

In the Table 4, (b), (i), and (r) represent baseline measurements, the end of zero-flow ischemia, and the end of reperfusion, respectively.

Left ventricular developed pressure (LVDP) and heart rate were equal in all groups (n=4/group) under baseline conditions prior to the onset of global ischemia. Ischemia caused a rapid cessation of cardiac rhythm in all groups of hearts. End developed pressure (EDP) was set to 7–10 cm $H_2O$ at the beginning of the perfusion period and increased in all the groups to a maximum after ~15 minutes of ischemia. While the non-diabetic control hearts had the greatest increase in end developed pressure during ischemia, the difference between groups was not significant.

Reperfusion of control and diabetic hearts resulted in limited functional recovery. LVDP and rhythmic activity did not recover in two of the diabetic controls (DC) and two of the control (C) hearts, with the average developed pressure after 60 minutes of reperfusion being 15±6 cm $H_2O$ in C and 20±10 cm $H_2O$ in DC hearts. Compared to the poor recovery of developed pressure in the C and DC hearts, zopolrestat treated diabetic hearts had significant functional recovery. Thus, aldose reductase inhibition in diabetic hearts improved functional recovery and reduced due to metabolic and ionic abnormalities ischemic injury after 20 minutes of global ischemia.

Creatine kinase release, a measure of myocardial injury and infarction, was significantly reduced during zero flow ischemia in the zopolrestat treated diabetic hearts. In DZ group release of CK was 156±39 IU/g dry wt in DZ compared to 396±36 IU/g dry wt in DC group.

Intracellular pH

Figure 8:
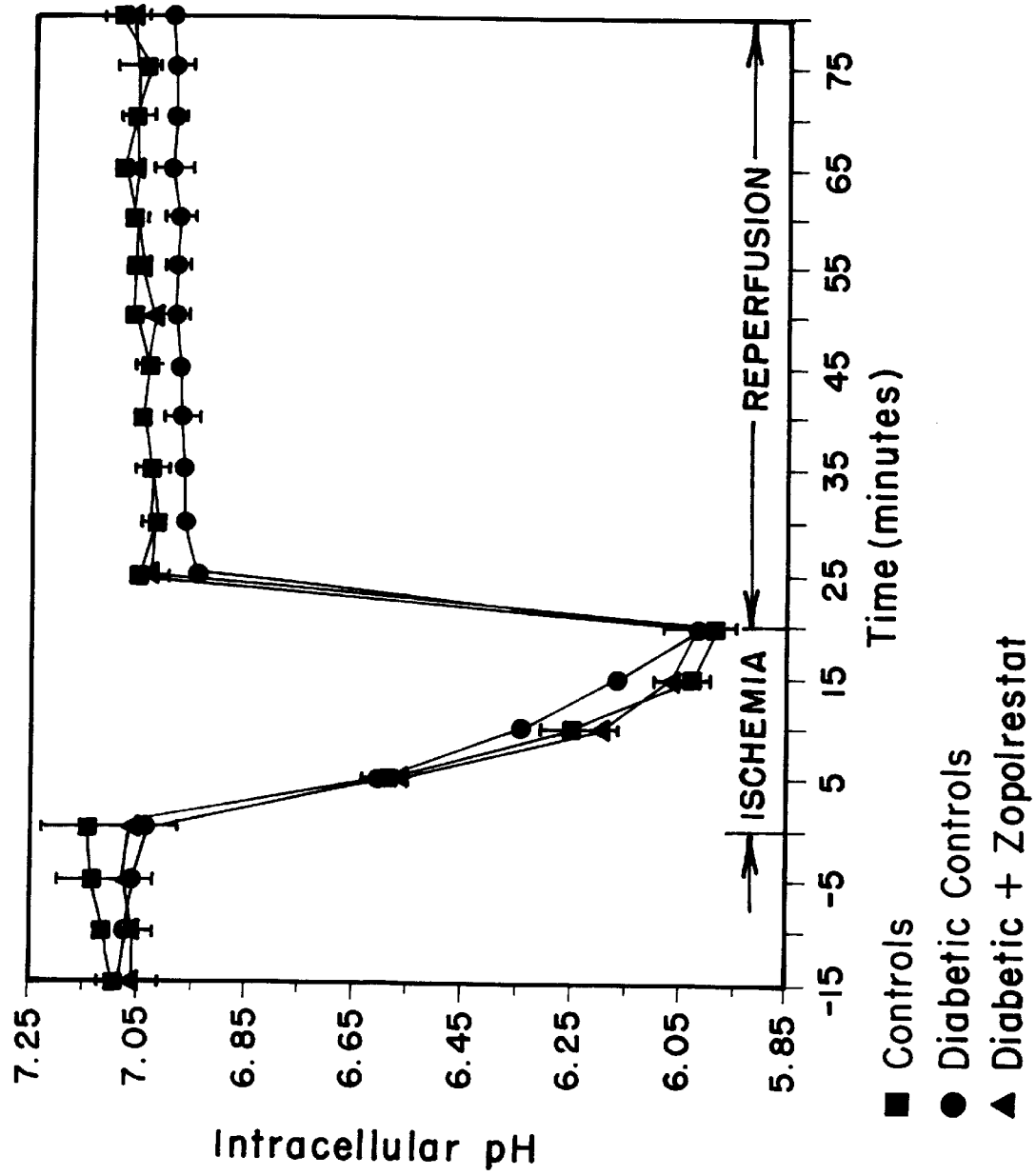
FIG. 8 is a graph showing changes in intracellular pH in diabetic controls, zopolrestat treated diabetic and non-diabetic control hearts during baseline, zero-flow ischemia and reperfusion conditions.

Intracellular pH was identical in all the groups at the beginning of the experiment and immediately before initiating global ischemia. FIG. 8 illustrates changes in intracellular pH during zero-flow ischemia and reperfusion in diabetic control (DC), zopolrestat treated diabetic (DZ), and non-diabetic control (C) hearts. Hearts were subjected to baseline (10 minutes), zero-flow ischemia (20 minutes), and reperfusion (60 minutes).

During the 20 minutes of zero-flow ischemia, the drop in pH was significant and similar in all groups, with the end-ischemic pH 5.98±0.04 in controls (C), 6.02±0.03 in diabetic controls (DC), 6.03±0.02 in diabetic treated with zopolrestat (DZ) hearts. The first five minutes of reperfusion resulted in normalization of pH to baseline values in all the groups except in DC hearts (pH of 7.01±0.02 was found in C, 6.99±0.04 in DZ, and 6.84±0.02 in DC). The rate of pH recovery in DC hearts was significantly slower than the other groups, requiring 10 minutes to return to baseline pH. This slower recovery is probably due to depressed activities of the $Na+$-$H^+$ exchanger and/or the $HCO_3$ dependent transporters.

High Energy Phosphates

Figure 9A:
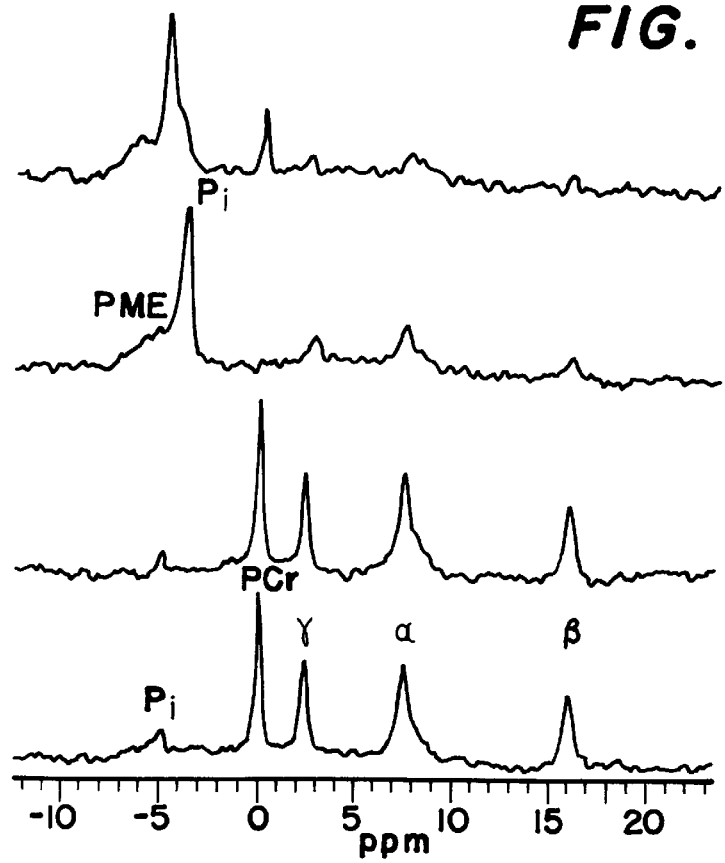
FIG. 9 are $^{31}$P NMR spectra of diabetic (FIG. 5A) and zopolrestat treated (FIG. 5B) hearts under baseline, before ischemia, zero-flow ischemia and at the end of reperfusion.
Figure 9B:
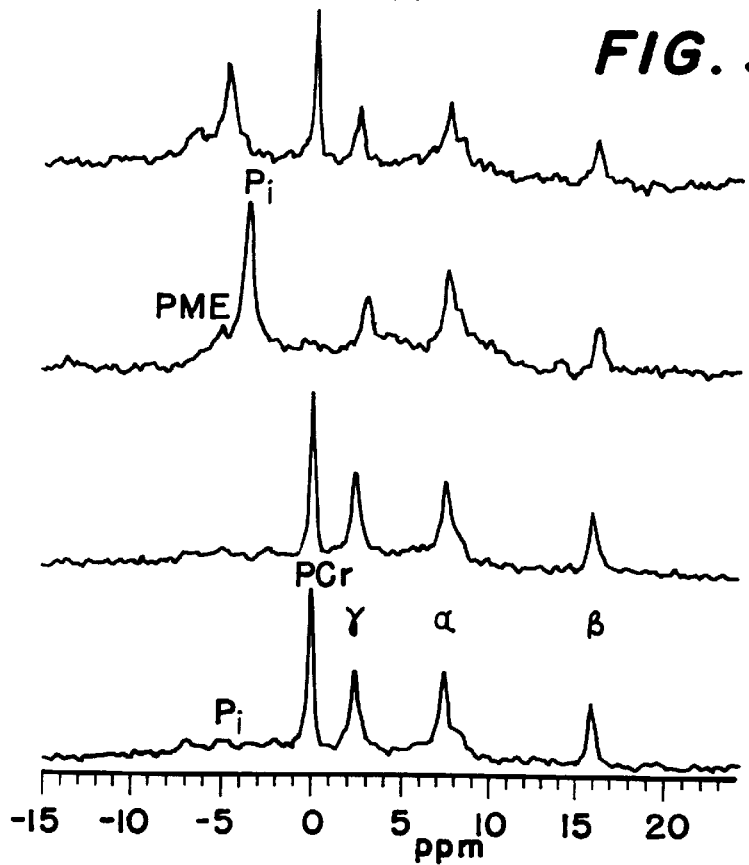

High energy phosphates were measured by $^{31}P$ NMP spectrometry as described in Example 5. Typical $^{31}P$ NMR spectra, collected every five minutes from DC and DZ hearts are shown in FIG. 9. The ratio of PCr/ATP was similar in all the groups of hearts prior to starting any intervention.

FIG. 9 are $^{31}P$ NMR spectra collected every five minutes from DC and DZ hearts. The ratio of PCr/ATP was similar in all the groups of hearts prior to starting any intervention. Spectra #2 from bottom in each stack were obtained prior to the start of ischemia. $P_i$ denotes intracellular inorganic phosphate resonance, while PCr and PME represent phosphocreatine and phosphomonoester resonances, respectively. The symbols a, β, and y represent resonances of ATP. FIG. 9 demonstrates that the recovery of PCr and ATP was greater in the zopolrestat (DZ) hearts than in the diabetic control hearts (DC) upon reperfusion.

Phosphocreatine

Figure 10:
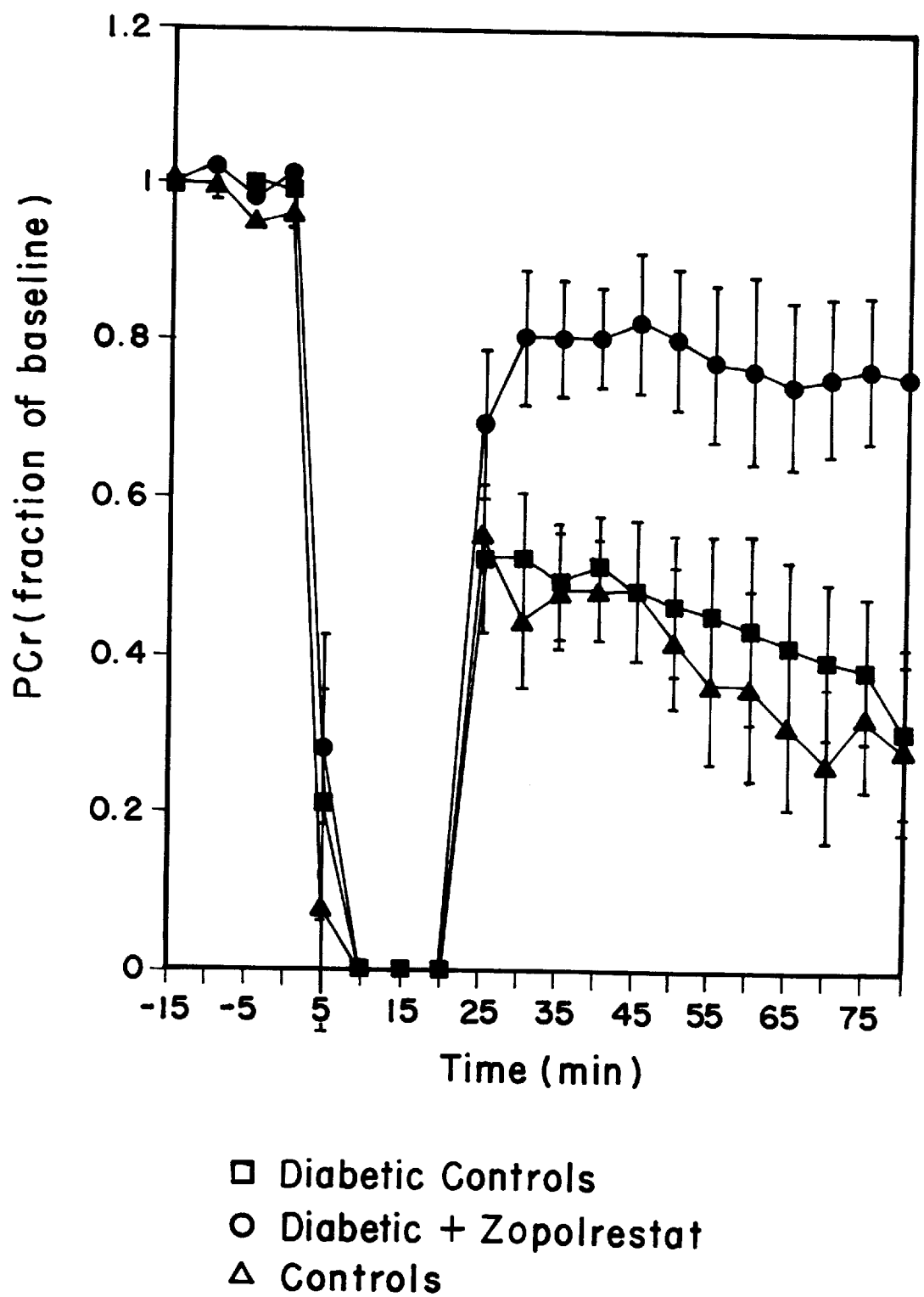
FIG. 10 is a graph showing changes in phosphocreatine during baseline, zero-flow ischemia and reperfusion in control diabetic and zopolrestat treated diabetic hearts.

FIG. 10 illustrates changes in phosphocreatine (PCr) during zero-flow ischemia. Changes in PCr are expressed as fraction of baseline, during 20 minutes of zero-flow ischemia and 60 minutes of reperfusion. Points represent data obtained every five minutes. PCr in zopolrestat treated hearts was found to be significantly greater than in DC and C hearts.

Phosphocreatine (PCr) fell rapidly and in a similar manner in all groups during the entire 20 minutes of zero of zero-flow ischemia. The levels of PCr (expressed as fraction of baseline) in the three groups after five minutes of ischemia were 0.26±0.04 in zopolrestat treated with diabetics (DZ), 0.21±0.03 in diabetic controls (DC), 0.24±0.05 in control (C) hearts. PCr was absent by 10 minutes of ischemia. Reperfusion caused a rapid but partial return of PCr in all four groups within five minutes as seen in FIG. 10. DC and C hearts had a progressive fall in PCr during the remainder of the reperfusion period, while the aldose reductase inhibited DZ hearts maintained PCr level during the reperfusion period. PCr levels at the end of the reperfusion period were significantly higher in the DZ hearts (0.75±0.08) compared to DC (0.36±0.06) and C (0.42±0.09) hearts. The greater recovery of PCr is consistent with reduced energy (ATP) utilization in the DZ hearts.

Adenosine Triphosphate (ATP)

Figure 11:
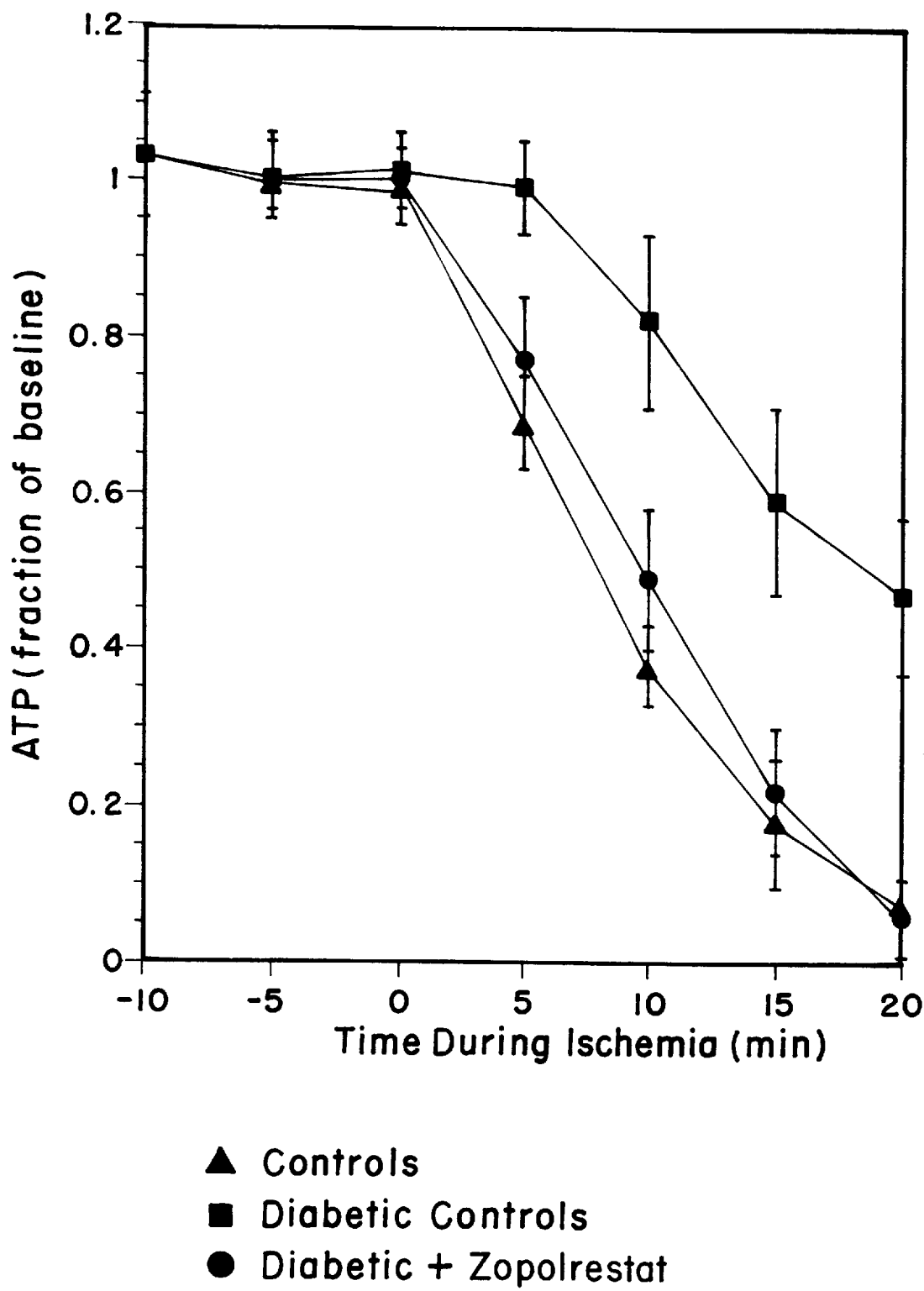
FIG. 11 is a graph showing changes in ATP during ischemia in control diabetic and zopolrestat treated diabetic hearts.

FIG. 11 illustrates changes in ATP during ischemia in the three groups of hearts. ATP in zopolrestat treated hearts was significantly greater than in DC and C hearts.

ATP, expressed as a fraction of baseline, was identical in all three groups prior to the start of zero-flow ischemia. Aldose reductase inhibition did not affect ATP levels in diabetic (DC) or non-diabetic (C) hearts prior to ischemia. The level of ATP was maintained during the first five minutes of ischemia in zopolrestat treated diabetics (DZ) hearts (fraction of baseline values were 0.99±0.06 and 0.93±0.06, respectively) while ATP fell significantly in C and DC hearts (fraction of baseline levels were 0.74±0.0.6 and 0.69±0.06 in DC and C hearts, respectively). During the next 15 minutes of ischemia, the decline in ATP levels was similar in DC and C, while in DZ hearts the decline in ATP was less pronounced. The end ischemic ATP levels were significantly higher in DZ than in other groups (fraction of baseline levels were 0.47±0.08 in DZ versus 0.06±0.02 in DC, 0.08±0.04 in C, 0.29±0.02 in Z). These results are consistent with increased production of ATP during ischemia via anaerobic glycolysis and/or reduced utilization of ATP-requiring processes.

Reperfusion resulted in ATP recovery which was significantly higher in DZ than in DC and C hearts. At the midpoint of reperfusion period, DZ hearts had significantly higher levels of ATP than other groups (fraction of baseline levels were 0.48±0.04 in DZ versus 0.06±0.02 in DC and 0.08±0.04 in C).

6. Low-flow Ischemia in Diabetic Hearts

Low-flow ischemia was induced to diabetic controls and to zopolrestat treated diabetic group as described in Example 4.

Intracellular-pH

Intracellular pH was identical in both groups at the beginning of the experiment and immediately before initiation of low-flow ischemia (flow set at 10% of baseline flow). Reduction of perfusate flow resulted in greater acidosis in DC hearts than in DZ hearts (n=2/group). At the end of 30 minutes of low-flow ischemia, the pH was $6.94^+0.02$ in DZ and 6.83±0.03 in DC hearts Reperfusion resulted in normalization of pH in both groups. The lower end-ischemic pH in DZ hearts may be indicative of either enhanced $H^+$ efflux or lower ATP utilization leading to lower $H^+$ production.

Phosphocreatine

Figure 12:
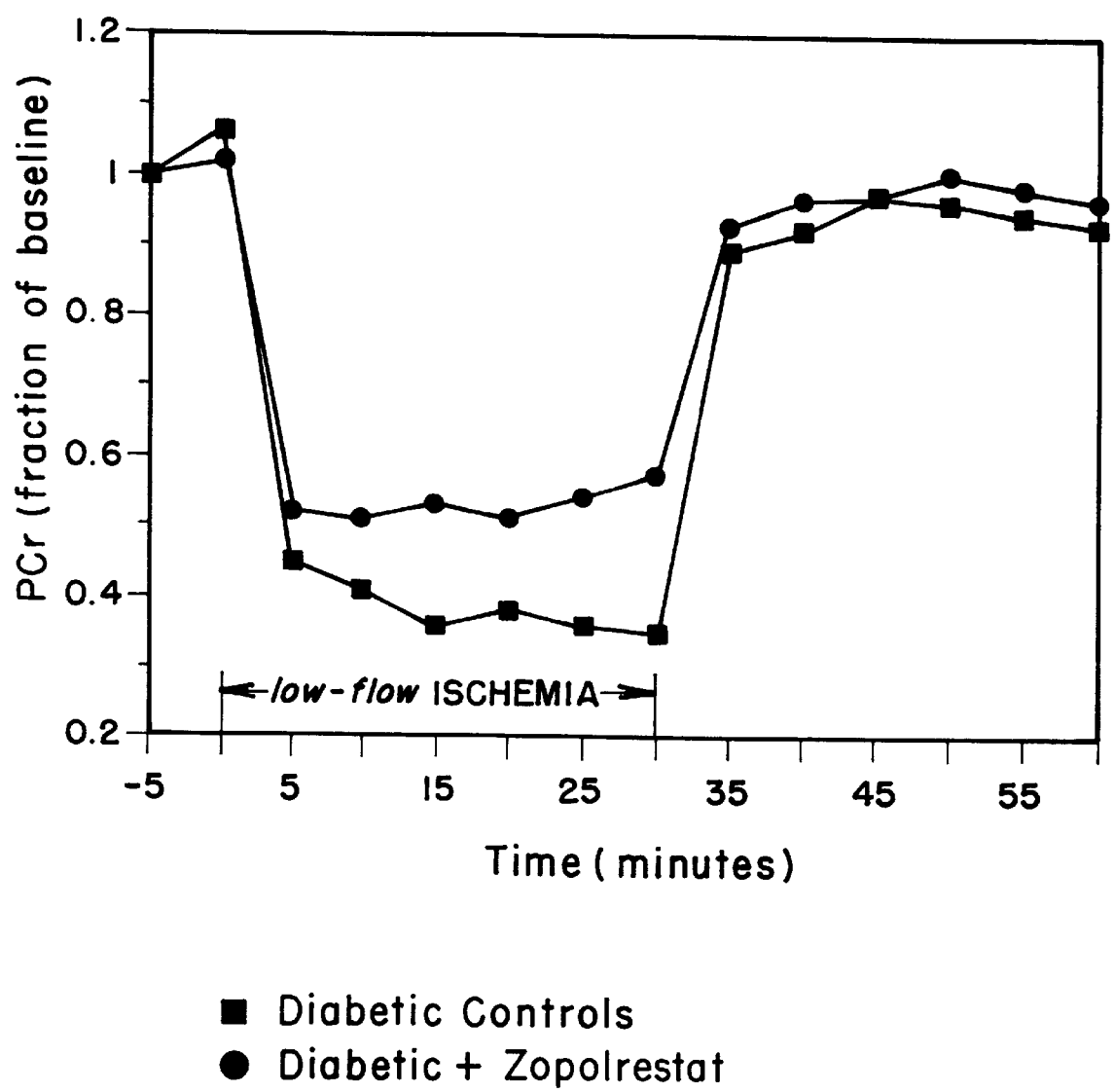
FIG. 12 is a graph showing changes in phosphocreatine during baseline, low-flow ischemia and reperfusion in diabetic controls and zopolrestat treated diabetic hearts.

FIG. 12 illustrates changes in PCr during low-flow ischemia. FIG. 12 shows changes in PCr, expressed as fraction of baseline, during 30 minutes of low-flow ischemia and 30 minutes of reperfusion. Points represent data obtained every five minutes.

Reductions in phosphocreatine PCr were greater in DC compared to DZ hearts during the 30 minutes of low-flow ischemia as seen in FIG. 12. The levels of PCr (expressed as fraction of baseline) in the two groups after 30 minutes of ischemia were 0.56±0.04 in DZ and 0.34±0.03 in DC hearts. PCr recovery was not different in the two groups on reperfusion.

Adenosine Triphosphate

Figure 13:
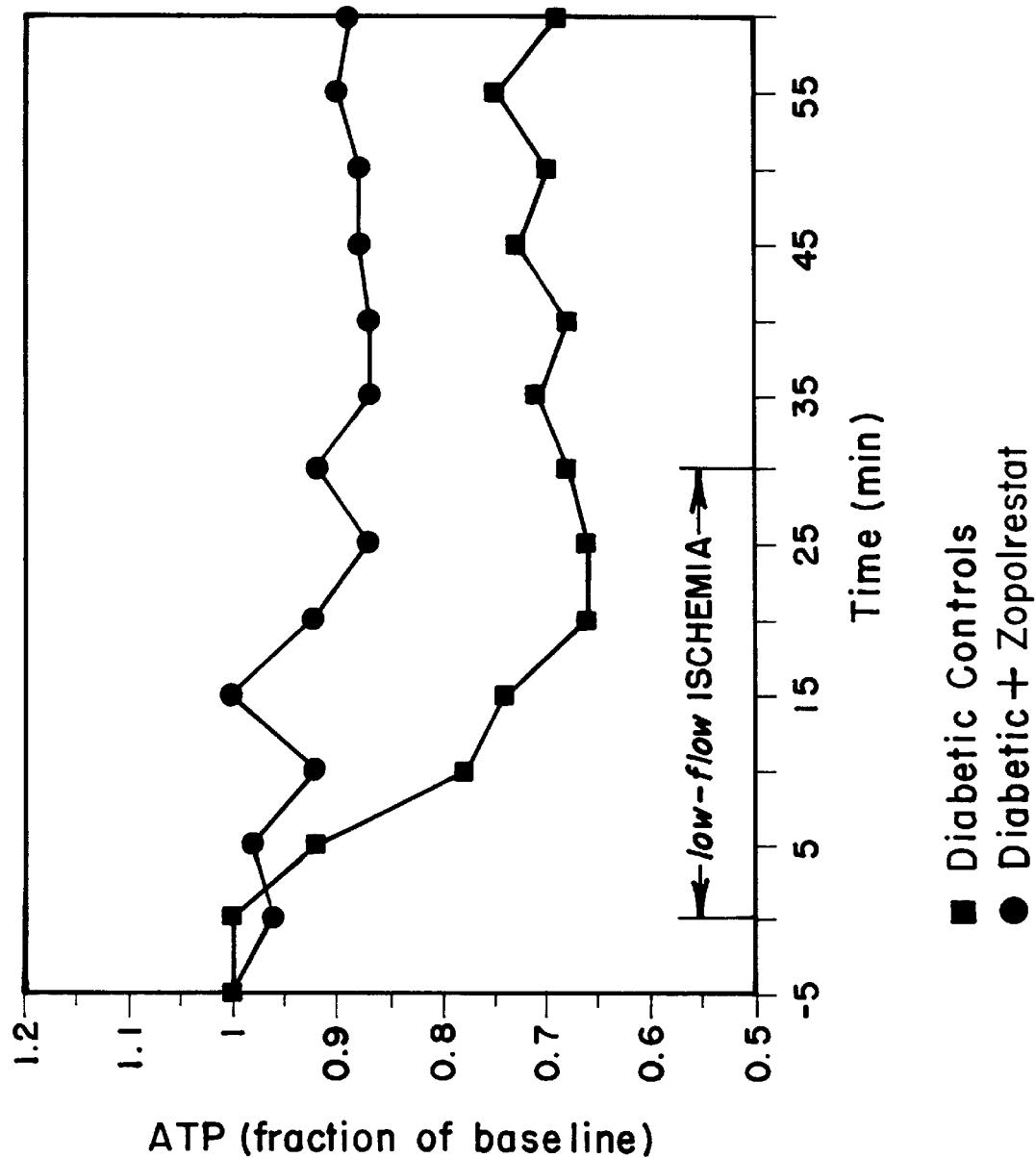
FIG. 13 is a graph showing changes in ATP during low-flow ischemia and reperfusion in diabetic controls and zopolrestat treated diabetic hearts.

FIG. 13 illustrates changes in ATP during low-flow ischemia. FIG. 13 shows changes in ATP, expressed as fraction of baseline, during 30 minutes of low-flow ischemia and 30 minutes of reperfusion period. Points represent data obtained every five minutes.

ATP fell progressively in DC hearts reaching values of 0.72±0.03 at the end of 30 minutes of low-flow ischemia, while in DZ hearts ATP was maintained at 0.89±0.05 during the same period (FIG. 13).

Maintenance of ATP in DZ hearts during low-flow ischemia is consistent with increased glycolysis compared to DC hearts.

The results obtained on the protective effects of aldose reductase inhibition during low-flow conditions show that increased glycolysis under low-flow conditions improves functional and metabolic recovery upon reperfusion. The myocardial protection observed in the aldose reductase inhibitor treated hearts subjected to zero-flow ischemia can be attributed to conserved ATP and the lower rise in sodium during ischemia.

7. Aldose Reductase Inhibitors Limit the Rise in Intracellular Free Calcium Levels During Ischemia To show that aldose reductase inhibition limits the rise in intracellular free calcium levels during ischemia and reperfusion, secondary to limiting the rise in intracellular sodium, intracellular calcium was measured in parallel with the $Na^+$, $K^+$-ATPase activity during baseline, ischemia, and reperfusion in zopolrestat treated and untreated diabetic hearts.

The measurements of intracellular calcium and $Na^+$, $K^+$-ATPase activity were obtained during baseline, ischemic (zero-flow), and reperfusion conditions in diabetic hearts perfused with and without the aldose reductase inhibitor zopolrestat. Using 5F-BAPTA and $^{19}F$ NMR spectroscopy intracellular calcium was measured in perfused hearts under the conditions stated above, while $Na^+$, $K^+$-ATPase activity was determined on freeze-clamped hearts using coupled-enzyme assays.

Aldose reductase inhibition via its influence on the $Na^+$, $K^+$-ATPase activity limits the rise in calcium during ischemia and reperfusion.

It is uncertain whether altered calcium homeostasis in diabetic hearts is entirely due to impaired $Na^+$-$C^{2+}$ exchanger function or is secondary to changes resulting from impaired $Na^+$, $K^+$-ATPase activity. Since it was found that aldose reductase inhibition normalizes $Na^+$, $K^+$-ATPase activity, thereby limiting increases in sodium and hence calcium, intracellular calcium was measured during baseline, zero-flow and low-flow ischemia, and reperfusion conditions in diabetic hearts perfused with and without the aldose reductase inhibitor, zopolrestat.

8. Intracellular Calcium Measurements of Zero-flow Ischemia

Intracellular calcium measurements were performed using 5F-BAPTA and $^{19}$F NMR spectroscopy in perfused diabetic hearts during zero-flow ischemia and during reperfusion. Typical $^{19}$F NMR spectra of 5F-BAPTA in perfused diabetic hearts are shown in FIG. 14A.

Figure 14A:
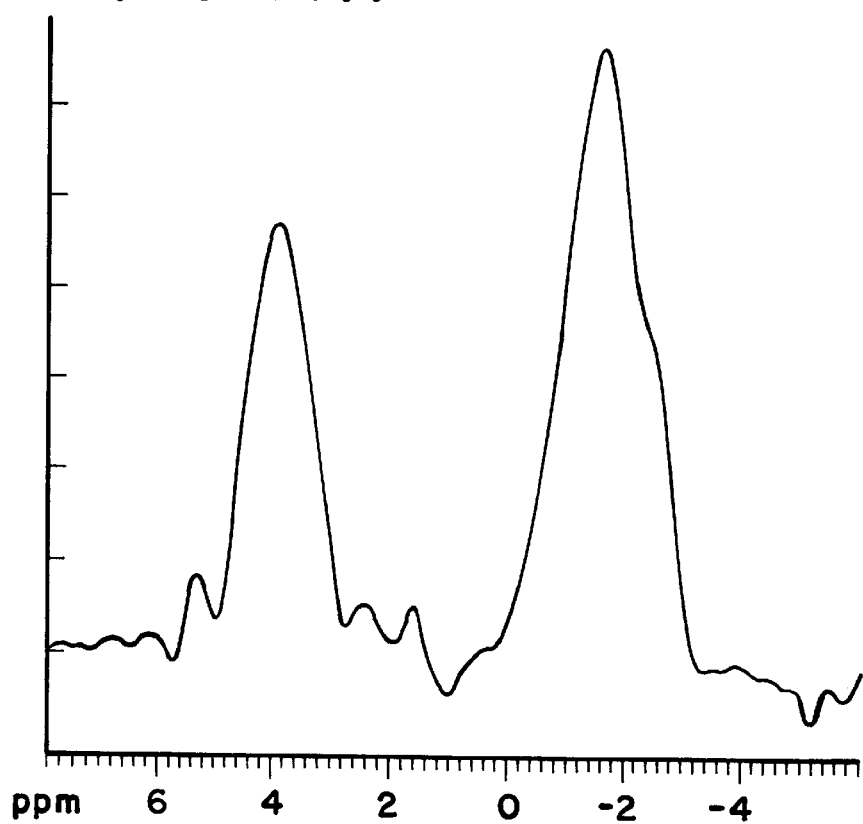
FIG. 14A is a $^{19}F$ NMR spectra of 5F-BAPTA perfused diabetic heart under baseline conditions.
Figure 14B:
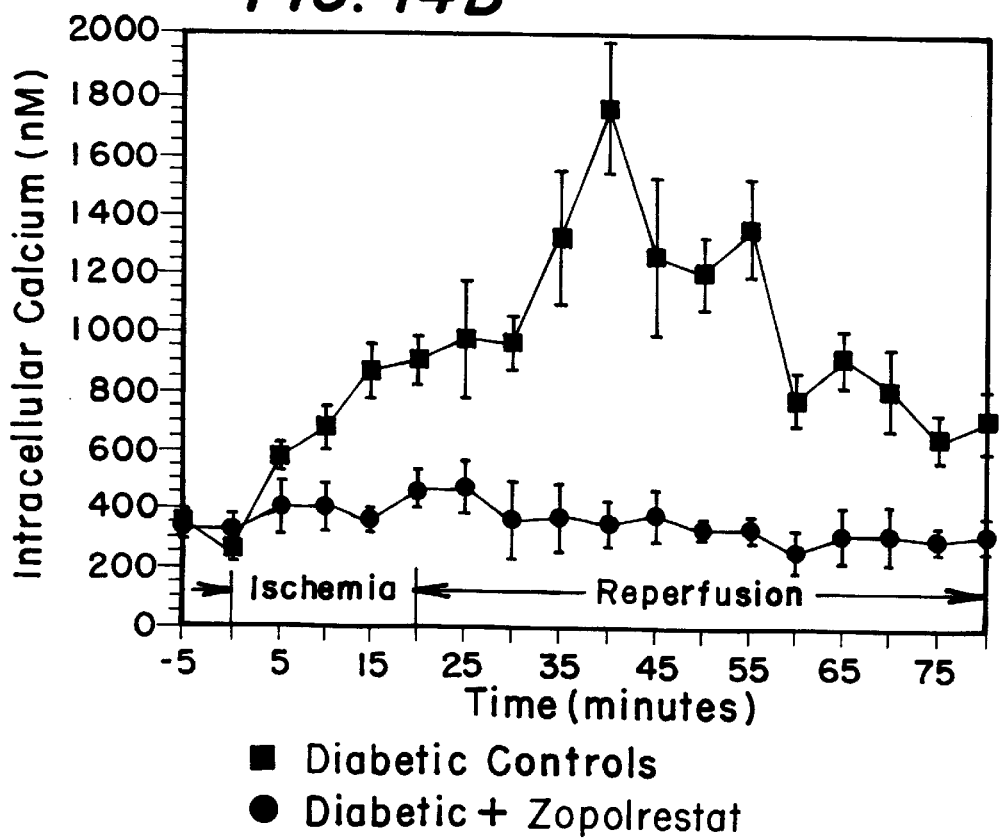
FIG. 14B is a graph showing changes in intracellular calcium observed during zero-flow ischemia and reperfusion in diabetic control and zopolrestat treated diabetic heart.

FIG. 14A show $^{19}$F NMR spectra of 5F-BAPTA perfused diabetic heart under baseline conditions. Changes in intracellular calcium observed during 20 minutes of zero-flow ischemia and 60 minutes of reperfusion are illustrated in FIG. 14B. Intracellular calcium was calculated using equations described in the examples.

The data presented in FIG. 14B demonstrates that zopolrestat lowers the rise in intracellular free Ca2+ during ischemia and enables intracellular calcium recovery during reperfusion. Intracellular calcium after 20 minutes of zero-flow ischemia was 869±81 nM and 465±64 nM (n=3 hearts in each group) in diabetic (DC) and zopolrestat treated (DZ) diabetic hearts, respectively. While calcium continued to remain elevated in diabetic control hearts, intracellular calcium in DZ hearts returned to pre-ischemic values. These observations are consistent with the findings that, in diabetic hearts, the protection against ischemia afforded by zopolrestat is mediated, in part, by preventing calcium overload.

Obtained data show that aldose reductase inhibition limits the rise in intracellular free calcium levels during ischemia and reperfusion, secondary to limiting the rise in intracellular sodium.

III. Method for Protecting the Heart and Heart Tissue and Amelioration of Damage Caused by Ischemic Insult The method according to the invention comprises administering to a subject in need of such a treatment a therapeutically effective amount of the active compound which reduces NADH/NAD$^+$ ratio and stimulates glycolysis to produce ATP, or a therapeutically effective amount of the inhibitor of sodium-potassium-chloride cotransporter or the pharmaceutically effective salt and ester thereof.

The active compounds comprise aldose reductase inhibitors such as zopolrestat, tolrestat, epolrestat, zenorestat, nicotinic acid, methylene blue, bumetanide, furosemide, piretanide, benzmetanide, and torasemide or any pharmaceutically acceptable acid addition salts and esters thereof.

The pharmaceutically acceptable salts, acid addition salts or esters of the compound of the invention can be prepared by methods known in the art in a conventional manner by treating a solution or suspension of the free base with about one chemical equivalent of a pharmaceutically acceptable acid or base. Concentration and recrystallization techniques are employed in isolating the salts are known in the art. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, sulfamic, sulfonic such as methanesulfonic, benzensulfonic, and related acids.

The compound will in general be administered to a patient so that an effective daily dose is received, generally a once a day dose between about 125 mg and 1250 mg, preferably a dose between about 125 and about 1000 mg per day. However, variation in dosage are expected depending on the compound, mode of administration and on the subject being treated.

The compound may be administered alone or in combination with other pharmaceutically acceptable excipients or carriers, in either single or multiple doses. Suitable pharmaceutical carriers include solid diluents or fillers, sterile aqueous solution and various organic solvents. A pharmaceutical composition formed by combining the compound of the invention and a pharmaceutically acceptable carrier or excipient can be readily administered in a variety of dosage forms such as tablets, powders, lozenges, syrups, injectable solutions and the like. These pharmaceutical compositions if suitable, contain additional ingredients such as flavorings, binders, excipients and the like. For purposes of the route of oral administration, tablets containing various excipients such as sodium citrate, calcium carbonate and calcium phosphate may be employed along with various disintegrants such as starch, alginic acid and certain complex silicates, together with binding agents, such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

In the preferred case, the compound will be administered parenterally. Parenteral solutions of the active compound may be employed in sesame or peanut oil, aqueous propylene glycol, or in sterile aqueous solution. Such aqueous solutions is preferably suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

UTILITY

This invention, which enhances myocardial function without the expense of metabolic deterioration would benefit patients with diabetes. The method for treatment according to the invention regulates intracellular sodium and calcium in normal and diabetic patients, thereby enabling these patients to function more normally and experience improved recovery from an ischemic insult.

The invention is useful for treatment of patients suffering from the myocardial disease, particularly those patients having developed condition leading to myocardial infarction, such as atherosclerosis, thrombotic diseases and normal coagulation disturbance. These patients are at risk of developing ischemia and because of the conditions discussed above, their survival depends on the degree and extent of the post-ischemic damage to the heart tissue. By administering immediately or as soon as possible after the ischemia, the therapeutic amount of compound of the invention, the extent of the damage of the heart tissue would be smaller, their survival higher and/or convalescence shorter. The timely treatment of these patients will decrease mortality and morbidity of the ischemic insult.

The method additionally is useful for the prevention of developing the ischemic damage as well as for limiting the extent of the heart tissue damage in patients who may be at risk of developing ischemia. These patients may be suffering from conditions leading to myocardial infarction or stroke, patients who may undergo surgery or another lengthy procedure where the ischemia may develop.

EXAMPLE 1

Diabetic Rats Model

This example describes diabetic rat model used for determination of conditions leading to a method for treatment and prevention of post-ischemic damage of the heart and heart tissue.

Spontaneously diabetic Bio-Bred (BB/W) rats from the colony maintained at the University of Massachusetts Medical Center, Worcester, were used in this study. BB/W rats have been chosen for the current study because the BB/W rats have been considered a useful model of autoimmune human insulin-dependent diabetes (IDDM). Like human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in *Diab. Metab. Rev.*, 8:9 (1992). The BB/W rats were 3–4 months old and weighed between 300–350g. The BB/W rats received daily insulin which was discontinued 24 hours prior to performing the isolated heart perfusion studies, leading to a hyperglycemic state.

These rats were acutely diabetic, receiving 2.02±0.04 units of insulin daily, and had been diabetic for at least 12±3 days. The mean blood glucose levels in these diabetic rats was 386±24 mg/dL The age-matched non-diabetic controls had mean blood glucose levels of 92±12 mg/dL.

EXAMPLE 2

Isolated Perfused Heart Model

This example describes an isolated perfused rat heart model used in development of this invention.

Studies were performed using an isovolumic isolated rat heart preparation. Acutely diabetic male BB/W rats and non-diabetic age-matched (3–4 months old) control were pretreated with heparin (1000 u; IP), followed by sodium pentobarbital (65 mg/kg; IP). After deep anesthesia was achieved as determined by the absence of a foot reflex, the hearts were rapidly excised and placed into iced saline The arrested heart were retrograde perfused in a non-recirculating model through the aorta within 2 minutes following their excision. Left ventricular developed pressure (LVDP) was determined using a latex balloon in the left ventricle with high pressure tubing connected to a pressure transducer. Perfusion pressure was monitored using high pressure tubing off the perfusion line. Hemodynamic measurements were recorded on a 4-channel Gould recorder. The system has two parallel perfusion lines with separate oxygenators, pumps and bubble traps, but common temperature control allowing rapid change perfusion media. The hearts were perfused using an accurate roller pump. The perfusate consisted of (in mM/L) NaCl 118, KCl 47, $CaCl_2$ 12, $MgCl_2$ 12, $NaHCO_3$ 25, and the substrate 11 mM glucose. The perfusion apparatus was tightly temperature controlled, with heated baths being used for the perfusate and for the water jacketing around the perfusion tubing to maintain heart temperature at 37°±5° C. under all conditions. The oxygenated perfusate in the room temperature reservoir was passed through 25 feet of thin-walled silicone tubing surrounded by distilled water at 37° C. saturated with 95% oxygen. The perfusate then entered the water jacketed (37° C.) tubing leading to the heart through a water jacketed bubble trap. This preparation provides excellent oxygenation that routinely has been stable for 3–4 hours.

EXAMPLE 3

Model for Zero-flow Ischemia

This example describes procedure used for study of zero-flow ischemia in diabetic control, diabetic treated, non-diabetic treated and control isolated hearts.

Diabetic control (DC) diabetic treated (DZ) normal (C) control and normal treated (CZ) hearts were subjected to 20 minutes of normoxic perfusion followed by 20 minutes of zero-flow ischemia where the perfusate flow is completely shut off, followed by 60 minutes of reperfusion.

Hearts were treated with 1 µm zopolrestat. In the zopolrestat-treated diabetic group (DZ), hearts were subjected to 10 minutes of normoxic perfusion with normal Krebs-Henseleit buffer and 10 minutes of normoxic perfusion with Krebs-Henseleit buffer containing 1 µm zopolrestat. The hearts were then subjected to 20 minutes of zero-flow ischemia followed by 60 minutes of reperfusion. In order to avoid any variability in reperfusion conditions, both DC and DZ hearts were reperfused with normal Krebs-Henseleit buffer.

EXAMPLE 4

Model for Low-flow Ischemia

This example describes procedure used for study of low-flow ischemia in diabetic controls, diabetic treated, non-diabetic treated and non-diabetic control isolated hearts.

Diabetic control hearts (DC) were subjected to 20 minutes of normoxic perfusion at a flow rate of 12.5 ml/min followed by 30 minutes of low-flow ischemia where the perfusate flow is slowed down to 1.25 ml/min, that is about 10% of normal perfusion, followed by 30 minutes of reperfusion at a normal flow rate (12.5 ml/min).

In the zopolrestat treated diabetic or non-diabetic groups (DZ or CZ), hearts were subjected to 10 minutes of normoxic perfusion (flow rate 12.5 ml/min) with normal Krebs-Henseleit buffer and 10 minutes of normoxic perfusion with Krebs-Henseleit buffer containing 1 µM zopolrestat. The hearts were subjected to 30 minutes of low-flow ischemia (flow rate 1.25 ml/min) and 30 minutes of reperfusion at normal flow rate (12.5 ml/min).

EXAMPLE 5

NMR Spectroscopy Methods for Determination of Intracellular pH, Sodium and Calcium This example describes specific spectroscopic procedures used for determination of intracellular sodium and intracellular calcium concentration, and intracellular pH.

All spectroscopy methods were performed on a Bruker AMX 400/or GE Omega-300 vertical bore spectrometer using a dual tuned probe.

$^{31}P$ NMR spectroscopy for Determination of Intracellular pH $^{31}P$ NMR spectroscopy was performed using 248 acquisitions of a 45 degree pulse and 1.21 second interpulse delay, with spectra processed using an exponential multiplication of 20 Hz and manual phasing. Intracellular pH was determined from the chemical shift of the $P_i$ resonance using a titration curve established in the laboratory for this purpose. All metabolites were referenced to their baseline value determined in duplicate at the start of the experiment and were expressed as a fraction of baseline.

$^{23}Na$ NMR Spectroscopy for Determination of Intracellular Sodium

Intracellular sodium concentration $[Na]_i$ was determined using the shift reagent thulium-$DOTP^{-5}$ according to *Magn. Reson. Med*, 15:33 (1990). This reagent was supplied by Magnetic Resonance Solutions, Dallas, Texas. Thulium-DOTP-5 has less hemodynamic effect on the heart and creates less line broadening, resulting in a more physiologic preparation and better resolution of the $[Na]_i$ resonance, especially under control conditions. Sodium spectra were acquired on the Bruker using the broad band probe tuned to 105.85 MHz. One thousand free induction decays were signal averaged over 5 minutes using 90 degree pulses with a +4000 Hz sweep width. $[Na]_i$ in mM was calculated from the calibrated area under the intracellular peak of the sodium spectrum.

Intracellular sodium concentration was calculated using the formula:

$$[Na]_i = \{[Anai]/[ANao]/\{(Vo/Vi)(fo/fi))[Nao]$$

where ANai and ANao are the intracellular and extracellular areas of the sodium resonances, Vo and Vi are the extracellular and intracellular volumes obtained from the TFM experiments, and fo and fi are the fractional visibilities of extra- and intracellular sodium (assumed to be 1.0 and 0.4, respectively).

$^{19}F$ NMR Spectroscopy for Determination of Intracellular Calcium

Intracellular calcium concentrations $[Ca]_i$, was measured after loading the heart with 5F-BAPTA, a compound that provides a signal proportional to the $[Ca^{2+}]_i$ according to Circ. Res, 68:1250 (1991). Hearts were perfused in the standard manner and then loaded with 5F-BAPTA over 1 hour. After perfusing the hearts with the acetoxymethyl ester of 5F-BAPTA (2.5 μM in normal perfusate) the hearts were perfused for 15 minutes with 5F-BAPTA-free perfusate to wash the 5F-BAPTA out of the extracellular space. Calcium concentration were 2.5 mM. The probe was tuned to 376.5 MHz (on the Bruker AMX-400 MHz spectrometer) and 1500 free induction decays were acquired in 5 minute intervals using 45 degree pulses and +5000 Hz sweep width. Intracellular calcium concentration in nM were calculated using the equation:

$$[Ca^{2+}]_i = Kd \times [Ca-5F-BAPTA]/[5F-BAPTA]$$

where Kd=500 nM and the ratio of calcium-bound to free [5F-BAPTA] is equal to the ratio of the corresponding peak areas of the two well defined peaks in the $^{19}F$ spectrum as described, ibid.

EXAMPLE 6

Methods Used for Measurements of Lactate and Pyruvate

This example describes methods used for measurements of lactate and pyruvate levels in post-ischemic hearts.

Parallel experiments were performed using hearts in each of the four groups and freeze-clamped prior to ischemia. Lactate and pyruvate were extracted from the freeze-clamped tissue using perchloric acid. Lactate and pyruvate were measured using standard biochemical assays published for example, in *Methods of Enzymatic Analysis Carbohydrates*, 570 (1984).

EXAMPLE 7

Methods Used for Measurements of Na$^+$, K$^+$-ATPase Activity

This example describes methods used for measurements of sodium or potassium ATPase activities.

Ouabain-sensitive Na$^+$, K$^+$-ATPase activities were measured in homogenates of diabetic (DC), zopolrestat treated diabetic (DZ), non-diabetic treated (CZ) and non-diabetic (C) hearts and expressed as pmol ADP formed/min/mg total protein by a spectrophotometric method previously described in *J. Lab. Clin. Med.*, 93:790 (1979). Heart tissue was homogenized at 4° C. in 2 ml of 0.2M sucrose-0.02M Tris-HCl buffer (pH 7.5) additionally containing protease inhibitor, 100 μl of 57 mM phenylmethylsulfonyl fluoride +10 μl of 1 mg/ml leupeptin, with a Polytron homogenizer for four periods, with each period not exceeding 15 seconds and then centrifuged at 100 g for 10 minutes at 4° C. The reaction was started by the addition of 20 μl of supernatant to a 1 ml ×1 cm cuvette containing in final concentration, 100 mM NaCl, 10 mM KCl, 2.5 mM MgCl$^2$, 2 mM EGTA, 1 mM Tris-ATP, 1 mM phosphoenolpyruvate, 30 mM imidazole-HCl buffer at pH 7.4, 0.15 mM NADH, 50 μg lactate dehydrogenase, 30 pg pyruvate kinase with or without 1 mM ouabain. After a 30 minute stabilization period, the linear rate of oxidation of NADH was monitored at 340 nm. ATPase activity was calculated from the linear portion of the curve using the mM extinction coefficient of NADH, volume of the reaction mixture, and the amount of heart shown below:

$$\text{ATPase activity} = \{islope(OD \text{ units/min})/622 \text{ (OD units ml/}\mu mol))\} \times \{1 \text{ ml/protein in mg}\}$$

Units are pmol ADP or Pi/min/mg total protein.

EXAMPLE 8

Method for Determination of Creatine Kinase

This example describes a method used to determine creatine kinase.

Creatine kinase (CK) was measured from timed 5 minute collections of the effluent for 1 hour of reperfusion following the ischemic period. Each 5 minute collection was analyzed for CK concentration using established methods currently employed in the laboratory according to the method described in *Circ. Res.*, 66:913 (1990). Total integrated CK activity was calculated for each heart. The integral of the CK release is an accurate measure of ischemic injury and this measurement complemented the NMR data.

EXAMPLE 9

Statistical Methods

This example illustrates statistical method used to process obtained experimental data.

Data were analyzed using INSTAT (GraphPad, San Diego, Calif.) software operating on an IBM compatible personal computer. Differences between different groups will be assessed using ANOVA for repeated measures, with subsequent Student-Newman-Keuls multiple comparisons post-tests if the p value for ANOVA is significant. A p value of less than 005 were used to reject the null hypothesis. All data was expressed as mean±SEM.

What is claimed is:

1. A method for protection of heart or heart tissue from damage caused by metabolic and ionic abnormalities developed during, following or associated with ischemia, said method comprising administering to a subject suffering from cardiac ischemia or following cardiac ischemia an effective amount of a compound which reduces NADH/NAD$^+$ ratio and stimulates glycolysis to produce ATP, or a pharmaceutically acceptable salt or ester thereof, wherein said compound is selected from the group selected from an aldose reductase inhibitor, nicotinic acid and methylene blue.

2. The method of claim 1 wherein the compound is the aldose reductase inhibitor.

3. The method of claim 2 wherein the aldose reductase inhibitor is selected from the group consisting of zopolrestat, tolrestat, epolrestat and zenorestat.

4. The method of claim 3 wherein the metabolic and ionic abnormalities of the heart tissue are caused by zero-flow ischemia.

5. The method of claim 4 wherein the compound is administered to the subject following a zero-flow ischemia event.

6. The method of claim 3 wherein the metabolic and ionic abnormalities of the heart tissue are caused by low-flow ischemia.

7. The method of claim 6 wherein the compound is administered to the subject following a low-flow ischemia event.

8. The method of claim 3 wherein the aldose reductase inhibitor is zopolrestat.

9. The method of claim 1 wherein the compound is nicotinic acid.

10. The method of claim 1 wherein the compound is methylene blue.

11. A method for amelioration of metabolic and ionic abnormalities causing damage of the heart tissue developed during or following cardiac ischemia, said method comprising a step of administering, during or after ischemic event, to a subject suffering from ischemic insult, a therapeutically cardioprotective amount of a compound which reduces NADH/NAD$^+$ ratio and stimulates glycolysis to produce ATP, or a pharmaceutically acceptable salt or ester thereof, wherein said compound is selected from the group consisting of an aldose reductase inhibitor, nicotinic acid and methylene blue.

12. The method of claim 11 wherein the compound is an aldose reductase inhibitor.

13. The method of claim 12 wherein the compound is the aldose reductase inhibitor selected from the group consisting of zopolrestat, tolrestat, epolrestat and zenorestat.

14. The method of claim 13, wherein the aldose reductase inhibitor is zopolrestat.

15. The method of claim 11, wherein the compound is nicotinic acid.

16. The method of claim 11, wherein the compound is methylene blue.

* * * * *